United States Patent

Von Deyn et al.

[11] Patent Number: 5,834,402
[45] Date of Patent: Nov. 10, 1998

[54] ISOXAZOLYLBENZOYL DERIVATIVES

[75] Inventors: Wolfgang Von Deyn, Neustadt; Regina Luise Hill, Speyer; Uwe Kardorff, Mannheim; Stefan Engel, Idstein; Martina Otten, Ludwigshafen; Marcus Vossen, Mannheim; Peter Plath, Frankenthal; Harald Rang, Altrip; Albrecht Harreus, Ludwigshafen; Franz Röhl, Schifferstadt; Helmut Walter, Obrigheim; Karl-Otto Westphalen, Speyer; Ulf Misslitz, Neustadt, all of Germany

[73] Assignee: BASF Aktiengesellschaft, Ludwigshafen, Germany

[21] Appl. No.: 894,481

[22] PCT Filed: Feb. 13, 1996

[86] PCT No.: PCT/EP96/00592

§ 371 Date: Aug. 22, 1997

§ 102(e) Date: Aug. 22, 1997

[87] PCT Pub. No.: WO96/26192

PCT Pub. Date: Aug. 29, 1996

[30] Foreign Application Priority Data

Feb. 24, 1995 [DE] Germany .................. 195 06 573.5

[51] Int. Cl.$^6$ ................. A01N 43/80; C07D 261/06; C07D 275/02

[52] U.S. Cl. ................ 504/271; 504/269; 548/240; 548/206

[58] Field of Search ................. 504/270, 271, 504/269; 548/240, 206

[56] References Cited

U.S. PATENT DOCUMENTS

| | | | |
|---|---|---|---|
| 5,480,857 | 1/1996 | Cramp et al. | 504/239 |
| 5,489,570 | 2/1996 | Geach et al. | 504/261 |
| 5,656,573 | 8/1997 | Roberts et al. | 504/271 |
| 5,658,858 | 8/1997 | Bailey et al. | 504/271 |

FOREIGN PATENT DOCUMENTS

| | | |
|---|---|---|
| 418 175 | 3/1991 | European Pat. Off. . |
| 609 797 | 8/1994 | European Pat. Off. . |

*Primary Examiner*—Deborah C. Lambkin
*Attorney, Agent, or Firm*—Keil & Weinkauf

[57] ABSTRACT

Isoxazol-4-ylbenzoyl derivatives of the formula I

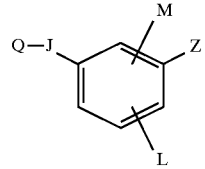

where the substituents have the meanings described in the specification;

and agriculturally customary salts thereof.

8 Claims, No Drawings

ISOXAZOLYLBENZOYL DERIVATIVES

This application is a 371 of PCT/EP96/00592 Feb. 13, 1996.

The present invention relates to novel herbicidally active isoxazolylbenzoyl derivatives, to processes for the preparation of the isoxazolylbenzoyl derivatives, to compositions comprising them, and to the use of these derivatives or of the compositions comprising them for controlling weeds.

The literature discloses herbicidally active isoxazolylbenzoyl derivatives, for example EP 609797.

European Patent Application EP-A-0 418 175 discloses 4-benzoyl-isoxazole derivatives which have herbicidal properties. The benzoyl group is not substituted by a heterocyclic group.

However, the herbicidal properties of the known compounds and the tolerance by crop plants are less than fully satisfactory.

It is an object of the present invention to find novel isoxazolylbenzoyl derivatives which have improved properties.

There have now been found novel isoxazolylbenzoyl derivatives of the formula I where the substituents have the following meanings:

L and M are hydrogen, $C_1$–$C_6$-alkyl, $C_2$–$C_6$-alkenyl, $C_2$–$C_6$-alkynyl, $C_1$–$C_4$-alkoxy, it being possible for these groups to be unsubstituted or substituted by one to five halogen atoms or $C_1$–$C_4$-alkoxy, or are halogen, cyano, nitro, a group —$(Y)_n$—$S(O)_m R^7$ or a group —$(Y)_n$—CO—$R^8$, is a 5- or 6-membered heterocyclic saturated or unsaturated radical which has one to three heteroatoms selected from the group consisting of oxygen, sulfur or nitrogen and which is unsubstituted or substituted by halogen, cyano, nitro, a group —CO—$R^8$, $C_1$–$C_4$-alkyl, $C_1$–$C_4$-haloalkyl, $C_3$–$C_8$-cycloalkyl, $C_1$–$C_4$-alkoxy, $C_1$–$C_4$-haloalkoxy, $C_1$–$C_4$-alkylthio, $C_1$–$C_4$-halo-alkylthio, di-$C_1$–$C_4$-alkylamino, phenyl which is unsubstituted or substituted by halogen, cyano, nitro, $C_1$–$C_4$-alkyl or $C_1$–$C_4$-haloalkyl, or an oxo group which may also exist as a hydroxyl group in the tautomeric form, or which forms a bicyclic system together with a fused phenyl ring which is unsubstituted or substituted by halogen, cyano, nitro, $C_1$–$C_4$-alkyl or $C_1$–$C_4$-haloalkyl, a fused carbocycle or a fused second heterocycle which is unsubstituted or substituted by halogen, cyano, nitro, $C_1$–$C_4$-alkyl, di-$C_1$–$C_4$-alkylamino, $C_1$–$C_4$-alkoxy, $C_1$–$C_4$-haloalkoxy or $C_1$–$C_4$-haloalkyl, Y is O or $NR^9$, n is zero or one, m is zero, one or two, $R^7$ is $C_1$–$C_4$-alkyl, $C_1$–$C_4$-haloalkyl or $NR^9 R^{10}$, $R^8$ $C_1$–$C_4$-alkyl, $C_1$–$C_4$-haloalkyl, $C_1$–$C_4$-alkoxy or $NR^9 R^{10}$, $R^9$ is hydrogen or $C_1$–$C_4$-alkyl, $R^{10}$ is $C_1$–$C_4$-alkyl, Q is an isoxazole ring which is linked in the 4-position, of the formula II where $R^1$ is hydrogen, $C_1$–$C_4$-alkyl or —$CO_2 R^3$, $R^2$ is hydrogen, $C_1$–$C_4$-alkyl or $C_3$–$C_6$-cycloalkyl, which can be unsubstituted or substituted by one or more halogen atoms or by $C_1$–$C_4$-alkyl and $R^3$ is $C_1$–$C_4$-alkyl, J is a carbonyl radical CO or a radical —$CHR^4$; and $R^4$ is an OH group, a hydroxyl group which may be acylated by $C_2$–$C_4$-acyl, or a chlorine atom;

and agriculturally customary salts of the compound I.

Compounds of the formula I where $R^1$ is H are obtained by acylating the β-keto esters of the formula A1 which are known per se [Y. Oikawa et al., JOC 43, 2087 (1978)] with a benzoic acid derivative of the formula III (T=Cl) to give an ester of the formula B1, converting this ester by reacting it with p-toluene-sulfonic acid in toluene to give a 1,3-diketone of the formula C1, thereupon either converting the 1,3-diketone C1 with triethyl orthoformate into an enol ether D1 or with dimethylformamide dimethyl acetal into an enamine D2, and reacting D1 or D2 with hydroxylamine to give the isoxazolylbenzoyl derivative of the formula I.a. The reaction sequence is compiled in the equation which follows:

Equation 1

D1: X = $OC_2 H_5$
D2: X = $N(CH_3)_2$

-continued
Equation 1

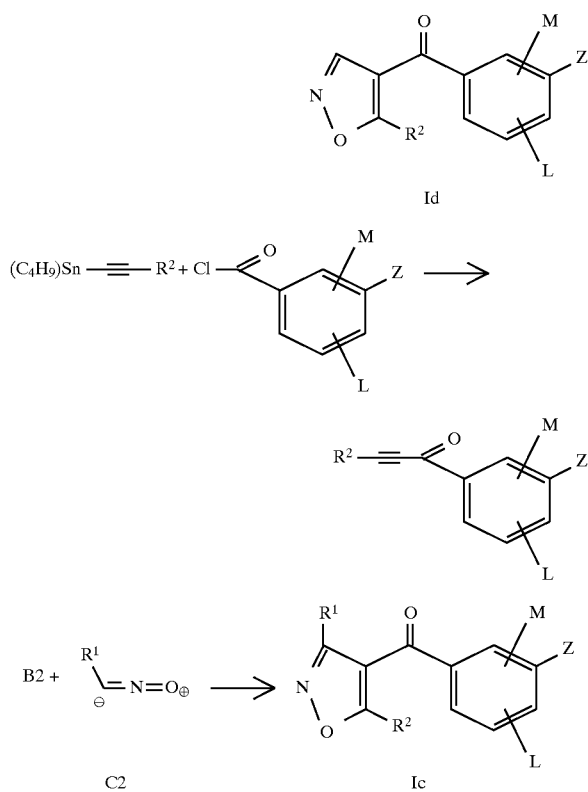

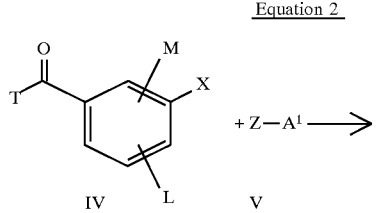

Benzoic acid derivatives of the formula III can be prepared as follows:

Benzoyl halides such as, for example, benzoyl chlorides of the formula III (T=Cl) are prepared in a manner known per se by reacting the benzoic acids of the formula III (T=OH) with thionyl chloride.

The benzoic acids of the formula III (T=OH) can be prepared in a known manner from the corresponding esters of the formula III (T=$C_1$–$C_4$-alkoxy) by acidic or alkaline hydrolysis.

The intermediates of the formula III can be synthesized for example in accordance with equations 2 and 3 via the routes described hereinbelow.

Equation 2

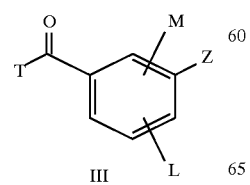

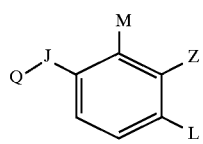

T is $C_1$–$C_4$-alkoxy, x is Cl, Br, I, —OS(O)$_2$CF$_3$, —OS(O)$_2$F, $A^1$ is Sn($C_1$–$C_4$-alkyl)$_3$, B(OH)$_2$, ZnHal, Hal being Cl or Br, and L, M and Z are as defined above.

Accordingly, the arylhalogen compounds or arylsulfonates IV can be reacted in a manner known per se with heteroaryl stannates (Stille couplings), heteroaryl/boron compounds (Suzuki couplings) or heteroaryl/zinc compounds (Negishi reaction) V (cf., for example, Synthesis 1987, 51–53, Synthesis 1992, 413) in the presence of a palladium or nickel transition metal catalyst and in the presence or absence of a base to give the novel compounds of the general formula III.

The benzoic acid derivatives of the formula III can also be obtained by reacting suitable bromine- or iodine-substituted compounds of the formula VI Equation 3

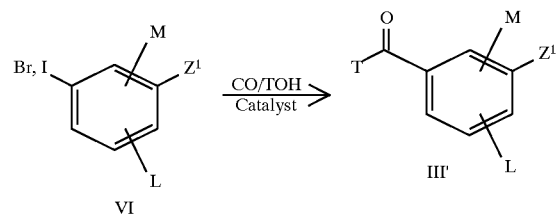

where $Z^1$ is Z or CN and $T^1$ is OH or $C_1$–$C_4$-alkoxy and where

L and M have the abovementioned meanings with carbon monoxide and water under elevated pressure in the presence of a palladium, nickel, cobalt or rhodium transition metal catalyst and of a base.

Preferred isoxazol-4-ylbenzoyl derivatives for the purposes of the present invention are those of the formula Ia

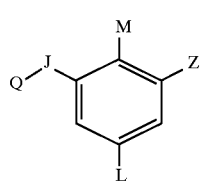

where

L is $C_1$–$C_6$-alkyl, $C_2$–$C_6$-alkenyl, $C_2$–$C_6$-alkynyl, $C_1$–$C_4$-alkoxy, $C_1$–$C_4$-alkylthio, $C_1$–$C_4$-haloalkyl, $C_1$–$C_4$-haloalkoxy, $C_1$–$C_4$-haloalkylthio, $C_1$–$C_4$-alkylsulfonyl, halogen, nitro or cyano and M is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-alkylthio, $C_1$–$C_4$-haloalkyl, $C_1$–$C_4$-haloalkoxy, $C_1$–$C_4$-haloalkylthio, $C_1$–$C_4$-alkylsulfonyl, halogen, nitro or cyano, and Q, J and Z have the abovementioned meanings.

Other preferred isoxazol-4-ylbenzoyl derivatives are those of the formula Ib where L and M are $C_1$–$C_6$-alkyl, $C_2$–$C_6$-alkenyl, $C_2$–$C_6$-alkynyl, $C_1$–$C_4$-alkoxy, $C_1$–$C_4$-alkylthio, $C_1$–$C_4$-haloalkyl, $C_1$–$C_4$-halo-alkoxy, $C_1$–$C_4$-haloalkylthio, $C_1$–$C_4$-alkylsulfonyl, halogen, nitro or cyano and Q, J and Z have the abovementioned meanings.

The catalysts nickel, cobalt, rhodium and, in particular, palladium can exist in the form of metals or in the form of customary salts, such as in the form of halogen compounds, eg. $PdCl_2$, $RhCl_3.H_2O$, acetates, eg. $Pd(OAc)_2$, cyanides and the like, at the known valency levels. There may also exist metal complexes with tertiary phosphines, metal alkyl carbonyls, metal carbonyls, eg. $CO_2(CO)_8$, $Ni(CO)_4$, metal carbonyl complexes with tertiary phosphines, eg. $(PPh_3)_2Ni(CO)_2$, or transition metal salts complexed with tertiary phosphines. The last-mentioned embodiment is particularly preferred when palladium is used as the catalyst. The type of phosphine ligands varies within a wide range. For example, they may be represented by the following formulae:

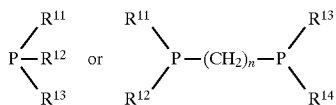

where n is a number 1, 2, 3 or 4 and the radicals $R^{11}$ to $R^{14}$ are low-molecular-weight alkyl, eg. $C_1$–$C_6$-alkyl, aryl, $C_1$–$C_4$-alkyl-aryl, eg. benzyl, phenethyl or aryloxy. Aryl is eg. naphthyl, anthryl and preferably substituted or unsubstituted phenyl. As regards the substituents, it is merely important that they are inert to the carboxylation reaction, but otherwise they can be varied within a broad range and comprise all inert C-organic radicals, such as $C_1$–$C_6$-alkyl radicals, eg. methyl, carboxyl radicals, such as COOH, COOM (M being, for example, an alkali metal, alkaline earth metal or ammonium salt), or C-organic radicals which are bonded via oxygen, such as $C_1$–$C_6$-alkoxy radicals.

The phosphine complexes can be prepared in a manner known per se, eg. as described in the documents mentioned at the outset. For example, customary commercially available metal salts, such as $PdCl_2$ or $Pd(OCOCH_3)_2$ are used as starting materials, and the phosphine, eg. $P(C_6H_5)_3$, $P(n-C_4H_9)_3$, $PCH_3(C_6H_5)_2$ or 1,2-bis(diphenylphosphino)ethane is added.

The amount of phosphine based on the transition metal is conventionally 0 to 20, in particular 0.1 to 10, mol equivalents, particularly preferably 1 to 5 mol equivalents.

The amount of transition metal is not critical. For cost reasons, however, a small amount, for example from 0.1 to 10 mol %, in particular 1 to 5 mol %, based on the starting material II or III, will rather be used.

To prepare the benzoic acids III (T=OH), the reaction is carried out using carbon monoxide and at least equimolar amounts of water, based on the starting materials VI. The reactant water can simultaneously also be used as the solvent, ie. the maximum amount is not critical.

Depending on the nature of the starting materials and the catalysts used, it may, however, also be advantageous to use, as the solvent, the base used for the carboxylation reaction or another inert solvent instead of the reactant.

Suitable inert solvents are solvents which are customary for carboxylation reactions, such as hydrocarbons, eg. toluene, xylene, hexane, pentane, cyclohexane, ethers, eg. methyl tert-butyl ether, tetrahydrofuran, dioxane, dimethoxyethane, substituted amides, such as dimethylformamide, persubstituted ureas, such as tetra-$C_1$–$C_4$-alkylureas, or nitriles, such as benzonitrile or acetonitrile.

In a preferred embodiment of the process, an excess of one of the reactants, in particular of the base, is used, so that an additional solvent can be dispensed with.

Bases which are useful for the process are all inert bases which are capable of binding the hydrogen iodide or hydrogen bromide which is liberated during the reaction. Examples are tertiary amines, such as tert-alkylamines, eg. trialkylamines, such as triethylamine, cyclic amines, such as N-methylpiperidine or N,N'-dimethylpiperazine, pyridine, alkali metal carbonates or alkali metal hydrogen carbonates, or tetraalkyl-substituted urea derivatives, such as tetra-$C_1$–$C_4$-alkylurea, eg. tetramethylurea.

The amount of base is not critical, 1 to 10, in particular 1 to 5 mol, conventionally being used. If the base is simultaneously used as the solvent, the amount is, as a rule, such that the reactants are dissolved. For reasons of practicality, unnecessarily high excesses are avoided in order to save costs, to be able to use small reaction vessels and to guarantee maximum contact between the reactants.

During the reaction, the carbon monoxide pressure is adjusted so that there is always an excess of CO based on VI. The carbon monoxide pressure is preferably 1 to 250 bar, in particular 5 to 150 bar, of CO at room temperature.

As a rule, the carbonylation reaction is carried out at from 20 to 250° C., in particular 30° to 150° C., either continuously or batchwise. In the case of batchwise operation, it is expedient to continuously inject carbon monoxide onto the reaction mixture in order to maintain a constant pressure.

The arylhalogen compounds VI which are used as starting compounds are known or can be prepared readily by a suitable combination of known syntheses.

For example, the halogen compounds VI can be obtained by Sandmeyer reaction from suitable anilines which, in turn, are synthesized by reducing suitable nitro compounds (cf., for example, in the case of VI where $Z_1$ is CN: Liebigs Ann. Chem. 1980, 768–778). The aryl bromides VI can additionally be obtained by direct bromination of suitable starting compounds [cf., for example, Monatsh. Chem. 99, 815–822 (1968)].

Equation 4

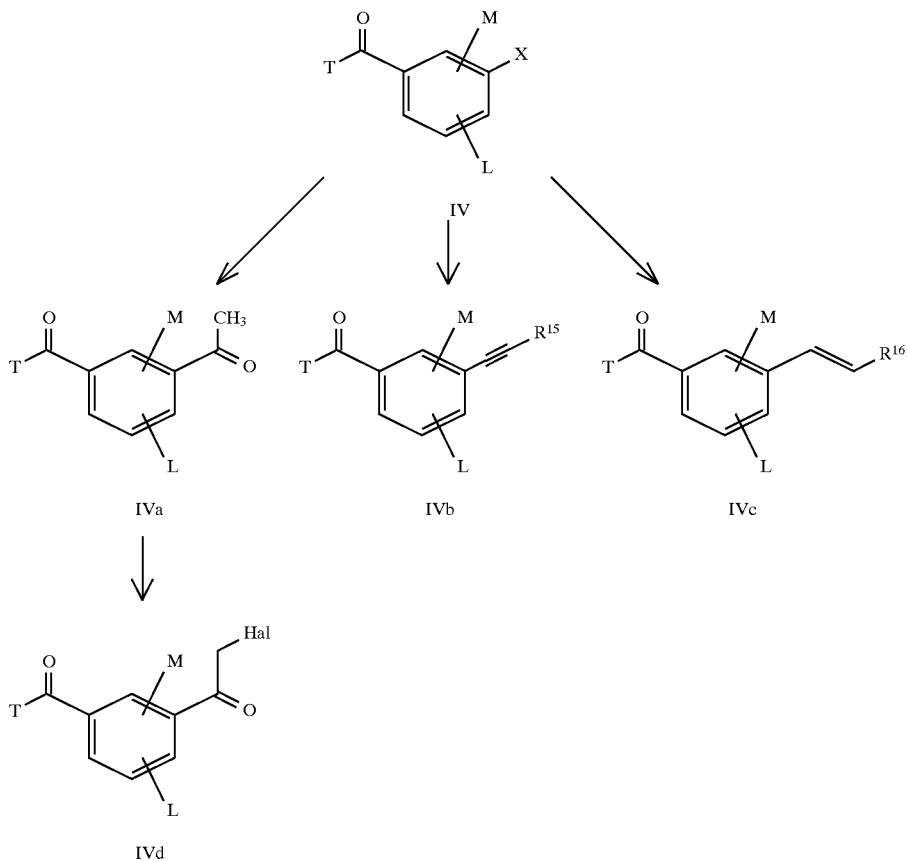

T is $C_1$–$C_4$-alkoxy,

X is Cl, Br, I, —OS(O)$_2$CF$_3$, —OS(O)$_2$F,

L, M and Z are as defined above, $R^{15}$ is hydrogen, $C_1$–$C_4$-alkyl, $C_1$–$C_4$-haloalkyl, $C_3$–$C_8$-cyclo-alkyl, or substituted or unsubstituted phenyl or trimethylsilyl, and $R^{16}$ is hydrogen, $C_1$–$C_4$-haloalkyl, $C_3$–$C_8$-cycloalkyl or substituted or unsubstituted phenyl.

Starting from the arylhalogen compounds or arylsulfonates IV, aryl methyl ketones IVa can be prepared in the presence of a palladium or nickel transition metal catalyst and in the presence or absence of a base by reaction with vinyl alkyl ethers followed by hydrolysis, in accordance with processes known from the literature [cf., for example, Tetrahedron Lett. 32, 1753–1756 (1991)].

The ethynylated aromatics IVb can be prepared in a manner known per se by reacting arylhalogen compounds or arylsulfonates IV with substituted acetylenes in the presence of a palladium or nickel transition metal catalyst (for example Heterocycles, 24, 31–32 (1986)). Derivatives IVb where $R^{15}$ is H are expediently obtained from the silyl compounds IVb in which $R^{15}$ is —Si(CH$_3$)$_3$ [J. Org. Chem. 46, 2280–2286 (1981)].

The arylalkenes IVc are obtained by subjecting arylhalogen compounds or arylsulfonates IV to a Heck reaction with olefins in the presence of a palladium catalyst (cf, for example, Heck, Palladium Reagents in Organic Synthesis, Academic Press, London 1985, or Synthesis 1993, 735–762).

Those benzoyl derivatives IV which are used as starting compounds and which are not already known [cf., for example, Coll. Czech. Chem. Commn. 40, 3009–3019 (1975)] can be prepared readily by a suitable combination of known syntheses.

For example, the sulfonates IV (X=—OS(O)$_2$CF$_3$, —OS(O)$_2$F) can be obtained from the corresponding phenols. Those corresponding phenols which are not already known (cf., for example, EP 195247) can be prepared by known methods (cf., for example, Synthesis 1993, 735–762).

The halogen compounds IV (X=Cl, Br or I) can be obtained, for example, from corresponding anilines by means of a Sandmeyer reaction.

Equation 5

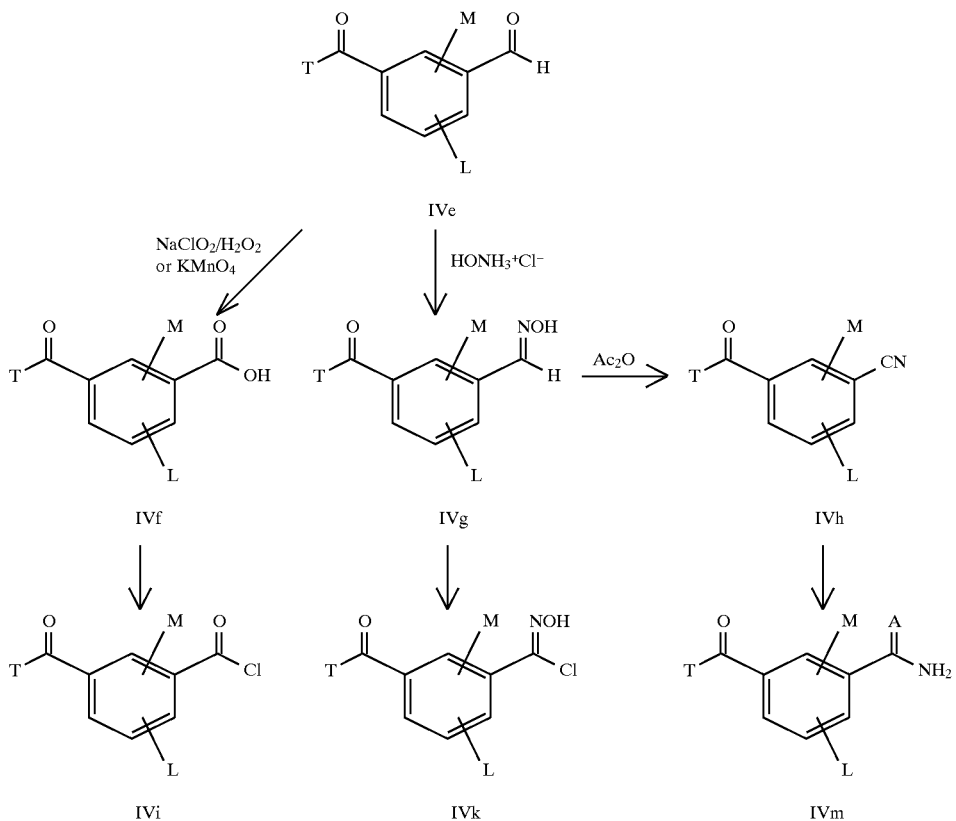

A is S, NH or NOH,

T is $C_1$–$C_4$-alkoxy and

L and M are as defined above.

Isophthalic acid derivatives IVf can be prepared from the aldehydes IVe by known processes [see J. March Advanced Organic Chemistry 3rd Ed., p. 629 et seq., Wiley-Interscience Publication (1985)].

The oximes IVg are advantageously obtained by reacting aldehydes IVe with hydroxylamine in a manner known per se [see J. March Advanced Organic Chemistry 3rd Ed., p. 805–806, Wiley-Interscience Publication (1985)].

The oximes IVg can be converted into nitriles IVh by processes which are also known per se [see J. March Advanced Organic Chemistry 3rd Ed., p. 931–932, Wiley-Interscience Publication (1985)].

Those aldehydes IVe which are required as starting compounds and which are not already known can be prepared by known methods. For example, they can be synthesized from the methyl compounds VII in accordance with equation 6.

Equation 6

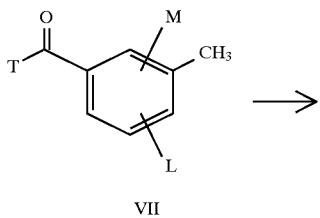

-continued

Equation 6

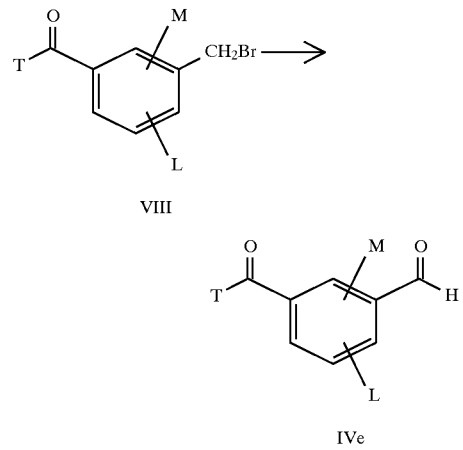

The radicals T, M and L have the meanings mentioned under equation 5. The methyl compounds VII can be reacted by generally known methods, for example with N-bromosuccinimide or 1,3-dibromo-5,5-dimethylhydantoin, to give the benzyl bromides VIII. The reaction of benzyl bromides to benzaldehydes IVe is also known from the literature [cf. Synth. Commun. 22 1967–1971 (1992)].

The precursors IVa to IVh are suitable for the synthesis of heterocyclic intermediates III.

For example, 5-oxazolyl derivatives [cf., for example, J. Heterocyclic Chem., 28, 17–28 (1991)] or 4-thiazolyl derivatives [cf., for example, Metzger, Thiazoles in: The Chemistry of heterocyclic compounds, Vol.34 p. 175 et seq. (1976)] can be obtained from the acetophenones IVa via the halogenated intermediate IVd.

The acetylenes IVb or the alkenes IVc are suitable for synthesizing 4-isoxazolyl, 5-isoxazolyl, 4,5-dihydroisoxazol-4-yl and 4,5-dihydroisoxazol-5-yl derivatives [cf., for example, Houben-Weyl, Methoden der organischen Chemie (Methods in Organic Chemistry), 4th Ed., Vol. X/3, p. 843 et seq. (1965)].

The benzoic acids IVf or the acid chlorides IVi which can be obtained therefrom by standard methods can be used for preparing 2-oxazolyl, 1,2,4-oxadiazol-5-yl, 1,3,4-oxadiazol-2-yl derivatives [cf., for example, J. Heterocyclic Chem., 28, 17–28 (1991)] or 2-pyrrolyl derivatives [cf., for example, Heterocycles 26, 3141–3151 (1987)], for example by processes known from the literature.

1,2,4-Triazol-3-yl derivatives can be prepared from benzonitriles IVh by conventional methods [cf., for example, J. Chem. Soc. 3461–3464 (1954)].

The benzonitriles IVh can be converted via the intermediate of the thioamides, amide oximes or amidines IVm to give 1,2,4-oxadiazol-3-yl [cf., for example, J. Heterocyclic Chem., 28, 17–28 (1991)], 2-thiazolyl, 4,5-dihydrothiazol-2-yl or 5,6-dihydro-4H-1,3-thiazin-2-yl derivatives [cf., for example, Houben-Weyl, Methoden der organischen Chemie (Methods in organic Chemistry), 4th Ed., Vol. E5, p. 1268 et seq. (1985)]. 1,2,4-Thiadiazol-5-yl derivatives [cf., for example, J. Org.Chem. 45 3750–3753 (1980)] or 1,3,4-thiadiazol-2-yl derivatives [cf., for example, J. Chem. Soc., Perkin Trans. I 1987–1991 (1982)] may also be obtained from the thioamides IVm (A=S) by processes known from the literature.

The oximes IVg can be converted into 3-isoxazolyl derivatives in a manner known per se via the intermediate of the hydroxamoyl chlorides IVk [cf., for example, Houben-Weyl, Methoden der organischen Chemie (Methods in Organic Chemistry), 4th Ed., Vol. X/3, p. 843 et seq. (1965)].

The compounds I where J is —CHR$^4$ can be obtained from the compounds of the formula Ib where J=CO by reducing them with sodium borohydride to give carbinols of the formula I.3 and reacting these either with methanesulfonyl chloride to give chlorides of the formula I.4 or acylating them with $C_2$–$C_4$-carboxylic acid anhydrides to to give esters of the formula I.5.

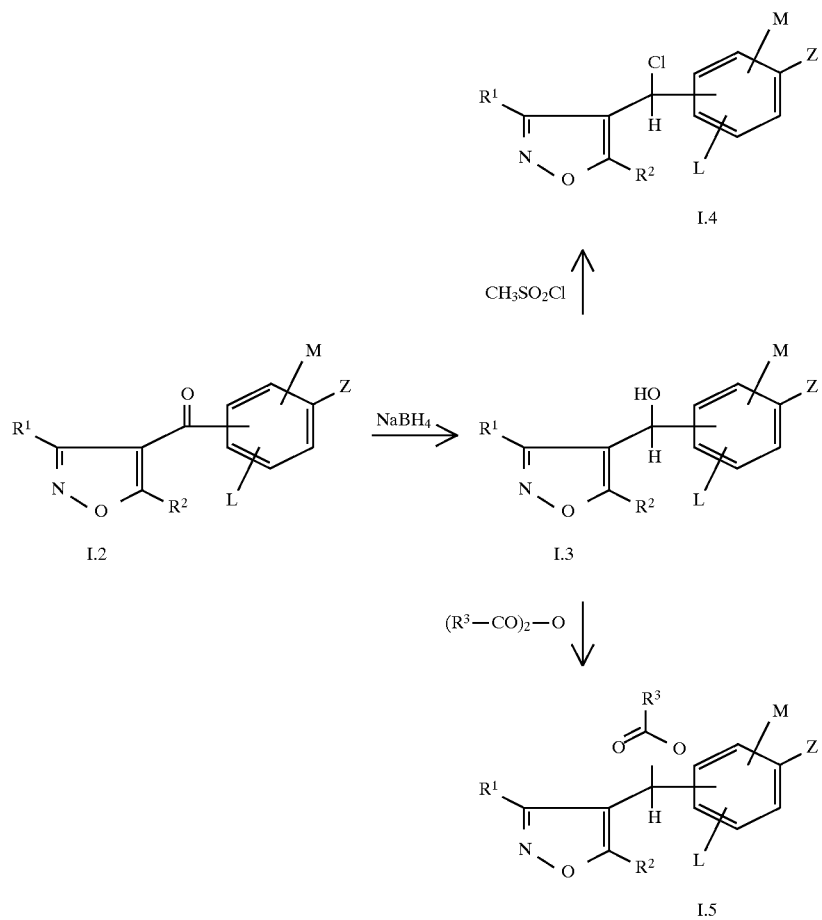

With regard to the intended use of the isoxazol-4-ylbenzoyl derivatives of the general formula I, the following radicals are suitable as substituents:

L and M are hydrogen,
$C_1$–$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2- dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 1,1,2-trimethylpropyl, 1,2,2-trimethylpropyl, 1-ethyl-1-methylpropyl or 1-ethyl-2-methyl-propyl, in particular methyl, ethyl, 1-methylethyl, 1-methylpropyl, 2-methylpropyl, 1,1-dimethylethyl and 1,1-dimethylpropyl;

$C_2$–$C_6$-alkenyl, such as 2-propenyl, 2-butenyl, 3-butenyl, 1-methyl-2-propenyl, 2-methyl-2-propenyl, 2-pentenyl, 3-pentenyl, 4-pentenyl, 3-methyl-2-butenyl, 1-methyl-2-butenyl, 2-methyl-2-butenyl, 1-methyl-3-butenyl, 2-methyl-4-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and ethyl-2-methyl-2-propenyl, in particular 1-methyl-2-propenyl, 1-methyl-2-butenyl, 1,1-dimethyl-2-propenyl and 1,1-dimethyl-2-butenyl;

$C_2$–$C_6$-alkynyl, such as propargyl, 2-butynyl, 3-butynyl, 2-pentynyl, 3-pentynyl, 4-pentynyl, 1-methyl-3-butynyl, 2-methyl-3-butynyl, 1-methyl-2-butynyl, 1,1-dimethyl-2 propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl;

$C_1$–$C_4$-alkoxy, such as methoxy, ethoxy, n-propoxy, 1-methylethoxy, n-butoxy, 1-methylpropoxy, 2-methylpropoxy and 1,1-dimethylethoxy, in particular $C_1$–$C_3$-alkoxy, such as methoxy, ethoxy and i-propoxy, it being possible for these groups to be unsubstituted or substituted by one to five halogen atoms, such as fluorine, chlorine, bromine and iodine, preferably fluorine and chlorine, or $C_1$–$C_4$-alkoxy as mentioned above.

The above-defined group —(Y)$_n$—S(O)$_m$R$^7$ is, for example, $C_1$–$C_4$-alkylthio, such as methylthio, ethylthio, n-propylthio, 1-methylethylthio, n-butylthio, 1-methylpropylthio, 2-methyl-propylthio and 1,1-dimethylethylthio, in particular methylthio;

$C_1$–$C_4$-alkylsulfinyl, such as methylsulfinyl, ethylsulfinyl, n-propylsulfinyl, 1-methylethylsulfinyl, n-butylsulfinyl, 1-methylpropylsulfinyl, 2-methylpropylsulfinyl and 1,1-dimethylethylsulfinyl, in particular methylsulfinyl;

$C_1$–$C_4$-alkylsulfonyl, such as methylsulfonyl, ethylsulfonyl, n-propylsulfonyl, 1-methylethylsulfonyl, n-butylsulfonyl, 1-methylpropylsulfonyl, 2-methylpropylsulfonyl and 1,1-dimethylethylsulfonyl, in particular methylsulfonyl;

$C_1$–$C_4$-alkoxysulfonyl, such as methoxysulfonyl, ethoxysulfonyl, n-propoxysulfonyl, 1-methylethoxysulfonyl, n-butoxysulfonyl, 1-methylpropoxysulfonyl, 2-methylpropoxysulfonyl and 1,1-dimethylethoxysulfonyl, in particular methoxysulfonyl;

N-$C_1$–$C_4$-alkylsulfamoyl, such as N-methylsulfamoyl, N-ethyl-sulfamoyl, N-n-propylsulfamoyl, N-1-methylethylsulfamoyl, N-n-butylsulfamoyl, N-1-methylpropylsulfamoyl, N-2-methyl-propylsulfamoyl and N-1,1-dimethylethylsulfamoyl, in particular N-methylsulfamoyl;

N-$C_1$–$C_4$-alkylsulfinamoyl, such as N-methylsulfinamoyl, N-ethylsulfinamoyl, N-n-propylsulfinamoyl, N-1-methylethyl-sulfinamoyl, N-n-butylsulfinamoyl, N-1-methylpropylsulfinamoyl, N-2-methylpropylsulfinamoyl and N-1,1-dimethylethylsulfinamoyl, n particular N-methylsulfinamoyl;

di-$C_1$–$C_4$-alkylsulfamoyl, such as dimethylsulfamoyl, diethyl-sulfamoyl, dipropylsulfamoyl, dibutylsulfamoyl, N-methyl-N-ethylsulfamoyl, N-methyl-N-propylsulfamoyl, N-methyl-N-1-methylethylsulfamoyl, N-methyl-N-1,1-dimethylethylsulfamoyl, di-1-methylethylsulfamoyl, N-ethyl-N-1-methylethylsulfamoyl and N-ethyl-N-1,1-dimethylethylsulfamoyl; in particular dimethylsulfamoyl;

di-$C_1$–$C_4$-alkylsulfinamoyl, such as dimethylsulfinamoyl, diethylsulfinamoyl, dipropylsulfinamoyl, dibutylsulfinamoyl, N-methyl-N-ethylsulfinamoyl, N-methyl-N-propylsulfinamoyl, N-methyl-N-1-methylethylsulfinamoyl, N-methyl-N-1,1-dimethyl-ethylsulfinamoyl, di-1-methylethylsulfinamoyl, N-ethyl-N-1-methylethylsulfinamoyl and N-Ethyl-N-1, 1-dimethylethylsulfin-amoyl; in particular dimethylsulfinamoyl, $C_1$–$C_4$-alkylsulfinyloxy, such as methylsulfinyloxy, ethyl-sulfinyloxy, n-propylsulfinyloxy, 1-methylethylsulfinyloxy, n-butylsulfinyloxy, 1-methylpropylsulfinyloxy, 2-methylpropyl-sulfinyloxy and 1,1-dimethylethylsulfinyloxy, in particular methylsulfinyloxy;

$C_1$–$C_4$-alkylsulfonyloxy, such as methylsulfonyloxy, ethyl-sulfonyloxy, n-propylsulfonyloxy, 1-methylethylsulfonyloxy, n-butylsulfonyloxy, 1-methylpropylsulfonyloxy, 2-methylpropyl-sulfonyloxy and 1,1-dimethylethylsulfonyloxy, in particular methylsulfonyloxy;

$C_1$–$C_4$-alkylsulfinylamino, such as methylsulfinylamino, ethylsulfinylamino, n-propylsulfinylamino, 1-methylethyl-sulfinylamino, n-butylsulfinylamino, 1-methylpropylsulfinylamino, 2-methylpropylsulfinylamino and 1,1-dimethylethylsulfinylamino, in particular methylsulfinylamino;

$C_1$–$C_4$-alkylsulfonylamino, such as methylsulfonylamino, ethylsulfonylamino, n-propylsulfonylamino, 1-methylethyl-sulfonylamino, n-butylsulfonylamino, 1-methylpropylsulfonylamino, 2-methylpropylsulfonylamino and 1,1-dimethylethylsulfonylamino, in particular methylsulfonylamino;

$N-C_1-C_4$-alkylsulfinyl-N-methylamino, such as N-methylsulfinyl-N-methylamino, N-ethylsulfinyl-N-methylamino, N-n-propylsulfinyl-N-methylamino, N-1-methylethylsulfinyl-N-methylamino, N-n-butylsulfinyl-N-methylamino, N-1-methylpropylsulfinyl-N-methylamino, N-2-methylpropylsulfinyl-N-methylamino and N-1,1-dimethylethyl-sulfinyl-N-methylamino, in particular N-methylsulfinyl-N-methylamino;

$N-C_1-C_4$-alkylsulfinyl-N-ethylamino, such as N-methylsulfinyl-N-ethylamino, N-ethylsulfinyl-N-ethylamino, N-n-propylsulfinyl-N-ethylamino, N-1-methylethylsulfinyl-N-ethylamino, N-n-butyl-sulfinyl-N-ethylamino, N-1-methylpropylsulfinyl-N-ethylamino, N-2-methylpropylsulfinyl-N-ethylamino and N-1,1-dimethylethyl-sulfinyl-N-ethylamino, in particular N-methylsulfinyl-N-ethylamino;

$N-C_1-C_4$-alkylsulfonyl-N-methylamino, such as N-methylsulfonyl-N-methylamino, N-ethylsulfonyl-N-methylamino, N-n-propylsulfonyl-N-methylamino, N-1-methylethylsulfonyl-N-methylamino, N-n-butylsulfonyl-N-methylamino, N-1-methylpropylsulfonyl-N-methylamino, N-2-methylpropylsulfonyl-N-methylamino and N-1,1-dimethylethylsulfonyl-N-methylamino, in particular N-methylsulfonyl-N-methylamino;

$N-C_1-C_4$-alkylsulfonyl-N-ethylamino, such as N-methylsulfonyl-N-ethylamino, N-ethylsulfonyl-N-ethylamino, N-n-propylsulfonyl-N-ethylamino, N-1-methylethylsulfonyl-N-ethylamino, N-n-butyl-sulfonyl-N-ethylamino, N-1-methylpropylsulfonyl-N-ethylamino, N-2-methylpropylsulfonyl-N-ethylamino and N-1,1-dimethylethyl-sulfonyl-N-ethylamino, in particular N-methylsulfonyl-N-ethylamino;

$C_1-C_4$-haloalkylthio, such as chloromethylthio, dichloromethylthio, trichloromethylthio, fluoromethylthio, difluoromethylthio, trifluoromethylthio, chlorofluoromethylthio, chlorodifluoromethylthio, 1-fluoroethylthio, 2-fluoroethylthio, 2,2-difluoroethylthio, 2,2,2-trifluoroethylthio, 2-chloro-2,2-difluoroethylthio, 2,2-dichloro-2-fluoroethylthio, 2,2,2-tri-chloroethylthio and pentafluoroethylthio, in particular trifluoromethylthio.

The above-defined group $—(Y)_n-CO—R^8$ is, for example, $C_1-C_4$-alkylcarbonyl, such as methylcarbonyl, ethylcarbonyl, n-propylcarbonyl, 1-methylethylcarbonyl, n-butylcarbonyl, 1-methylpropylcarbonyl, 2-methylpropylcarbonyl and 1,1-dimethylethylcarbonyl, in particular methylcarbonyl;

$C_1-C_4$-alkoxycarbonyl, such as methoxycarbonyl, ethoxycarbonyl, n-propoxycarbonyl, 1-methylethoxycarbonyl, n-butoxycarbonyl, 1-methylpropoxycarbonyl, 2-methylpropoxycarbonyl and 1,1-dimethylethoxycarbonyl, in particular methoxycarbonyl;

$N-C_1-C_4$-alkylcarbamoyl, such as N-methylcarbamoyl, N-ethyl-carbamoyl, N-n-propylcarbamoyl, N-1-methylethylcarbamoyl, N-n-butylcarbamoyl, N-1-methylpropylcarbamoyl, N-2-methyl-propylcarbamoyl and N-1,1-dimethylethylcarbamoyl, in particular N-methylcarbamoyl;

di-$C_1-C_4$-alkylcarbamoyl, such as dimethylcarbamoyl, diethyl-carbamoyl, dipropylcarbamoyl, dibutylcarbamoyl, N-methyl-N-ethylcarbamoyl, N-methyl-N-propylcarbamoyl, N-methyl-N-1-methylethylcarbamoyl, N-methyl-N-1,1-dimethylethylcarbamoyl, di-1-methylethylcarbamoyl, N-ethyl-N-1-methylethylcarbamoyl and N-ethyl-N-1,1-dimethylethylcarbamoyl; in particular dimethylcarbamoyl;

$C_1-C_4$-alkylcarbonyloxy, such as methylcarbonyloxy, ethyl-carbonyloxy, n-propylcarbonyloxy, 1-methylethylcarbonyloxy, n-butylcarbonyloxy, 1-methylpropylcarbonyloxy, 2-methylpropyl-carbonyloxy and 1,1-dimethylethylcarbonyloxy, in particular methylcarbonyloxy;

$C_1-C_4$-alkylcarbonylamino, such as methylcarbonylamino, ethyl-carbonylamino, n-propylcarbonylamino, 1-methylethylcarbonylamino, n-butylcarbonylamino, 1-methylpropylcarbonylamino, 2-methyl-propylcarbonylamino and 1,1-dimethylethylcarbonylamino, in particular methylcarbonylamino;

$N-C_1-C_4$-alkylcarbonyl-N-methylamino, such as N-methylcarbonyl-N-methylamino, N-ethylcarbonyl-N-methylamino, N-n-propylcarbonyl-N-methylamino, N-1-methylethylcarbonyl-N-methylamino, N-n-butylcarbonyl-N-methylamino, N-1-methylpropylcarbonyl-N-methylamino, N-2-methylpropylcarbonyl-N-methylamino and N-1,1-dimethylethyl-carbonyl-N-methylamino, in particular N-methylcarbonyl-N-methylamino.

Z is, for example, a 5- or 6-membered heterocyclic saturated or unsaturated radical which contains one to three hetero atoms selected from the group consisting of oxygen, sulfur or nitrogen, for example a five-membered heteroaromatic ring such as 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,3,4-oxadiazol-2-yl, 1,2,3-oxadiazol-4-yl, 1,2,3-oxadiazol-5-yl, 1,2,5-oxadiazol-3-yl, 1,2,4-thiadiazol-3-yl, 1,2,4-thiadiazol-5-yl, 1,3,4-thiadiazol-2-yl, 1,2,3-thiadiazol-4-yl, 1,2,3-thiadiazol-5-yl, 1,2,5-thiadiazol-3-yl, 1,2,4-triazol-3-yl, 1,3,4-triazol-2-yl,1,2,3-triazol-4-yl, 1,2,3-triazol-5-yl, 1,2,4-triazol-5-yl, tetrazol-5-yl, in particular 2-thiazolyl and 3-isoxazolyl;

a six-membered heteroaromatic ring, such as 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-5-yl and 1,2,4-triazin-3-yl, 1,2,4-triazin-6-yl, 1,2,4,5-tetrazin-3-yl;

a 5- to 6-membered saturated or partially unsaturated heterocycle which has one to three nitrogen atoms and/or one or two oxygen or sulfur atoms, such as 2-tetrahydrofuranyl, 3-tetrahydrofuranyl, 2-tetrahydrothienyl, 3-tetrahydrothienyl, tetrahydrothiopyran-2-yl, tetrahydrothiopyran-3-yl, tetrahydrothiopyran-4-yl, 1,3-dithiolan-2-yl, 1,3-dithiolan-4-yl, 1-3-dithian-2-yl, 1,3-dithian-4-yl, 5,6-dihydro-4H-1,3-thiazin-2-yl, 1,3-oxathiolan-2-yl, 1,3-oxathian-2-yl, 1-pyrrolidinyl, 2-pyrrolidinyl, 3-pyrrolidinyl, 3-isoxazolidinyl, 4-isoxazol-idinyl, 5-isoxazolidinyl, 3-isothiazolidinyl, 4-isothiazolidinyl, 5-isothiazolidinyl, 3-pyrazolidinyl, 4-pyrazolidinyl, 5-pyrazoli-dinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2,3-pyrrolin-2-yl, 2,3-pyrrolin-3-yl, 2,4-pyrrolin-2-yl, 2,4-pyrrolin-3-yl, 2,3-isoxazolin-3-yl, 3,4-isoxazolin-3-yl, 4,5-isoxazolin-3-yl, 2,3-isoxazolin-4-yl, 3,4-isoxazolin-4-yl, 4,5-isoxazolin-4-yl, 2,3-isoxazolin-5-yl, 3,4-isoxazolin-5-yl, 4,5-isoxazolin-5-yl, 2,3-isothiazolin-3-yl, 3,4-isothiazolin-3-yl, 4,5-isothiazolin-3-yl, 2,3-isothiazolin-4-yl, 3,4-isothiazolin-4-yl, 4,5-isothiazolin-4-yl, 2,3-isothiazolin-5-yl, 3,4-isothiazolin-5-yl, 4,5-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 4,5-dihydrooxazol-2-yl, 4,5-dihydrooxazol-4-yl, 4,5-dihydrooxazol-5-yl, 1,3-dioxolan-2-yl, 1,3-dioxolan-4-yl, 1,3-dioxan-5-yl, 1,4-dioxan-2-yl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydro-triazin-2-yl and 1,2,4-tetrahydrotriazin-3-yl, in particular 2-tetrahydrofuranyl, 1,3-dioxolan-2-yl and 1,3-dioxan-2-yl, and which is unsubstituted or substituted by halogen as mentioned above, in particular fluorine or chlorine, cyano, nitro, a group —COR$^8$, for example alkylcarbonyl as mentioned above, alkoxycarbonyl as mentioned above, N-alkylcarbamoyl as mentioned above, dialkylcarbamoyl as mentioned above;

$C_1$–$C_4$-alkyl as mentioned above, $C_1$–$C_4$-haloalkyl, such as, for example, chloromethyl, difluoromethyl, dichloromethyl, trifluoromethyl, trichloromethyl, chlorodifluoromethyl, 1-fluoroethyl, 2-fluoroethyl, 2,2-difluoroethyl, 1,1,2,2-tetrafluoroethyl, 2,2,2-trifluoroethyl, 2-chloro-1,1,2-trifluoroethyl and pentafluoroethyl, decafluorobutyl, 1,1-bis-trifluoromethyl-2,2,2-trifluoroethyl, preferably difluoromethyl, trifluoromethyl, trichloromethyl and chlorodifluoromethyl;

$C_3$–$C_8$-cycloalkyl, such as, for example, cyclopropyl, cyclobutyl, cyclopentyl, cyclohexyl, cycloheptyl, cyclooctyl, in particular cyclopropyl and cyclohexyl;

$C_1$–$C_4$-alkoxy as mentioned above, $C_1$–$C_4$-haloalkoxy, such as, for example, chloromethoxy, dichloromethoxy, trichloromethoxy, fluoromethoxy, difluoromethoxy, trifluoromethoxy, chlorodifluoromethoxy, dichlorofluoromethoxy, 1-fluoromethoxy, 2-fluoroethoxy, 2,2-difluoroethoxy, 1,1,2,2-tetrafluoroethoxy, 2,2,2-trifluoroethoxy, 2-chloro-1,1,12-trifluoroethoxy and pentafluoroethoxy, in particular $C_1$–$C_3$-haloalkoxy, such as 2,2,2-trifluoroethoxy and 2-chloro-2,2-difluoroethoxy;

$C_1$–$C_4$-alkylthio as mentioned above, $C_1$–$C_4$-haloalkylthio as mentioned above, di-$C_1$–$C_4$-alkylamino, such as, for example, dimethylamino, diethylamino, dipropylamino, dibutylamino, N-methyl-N-ethylamino, N-methyl-N-propylamino, N-methyl-N-1-methylethylamino, N-methyl-N-1,1-dimethylethylamino, di-1-methylethylamino, N-ethyl-N-1-methylethylamino and N-ethyl-N-1,1-dimethylethylamino;

optionally substituted phenyl, or an oxo group which may also exist as a hydroxyl group in the tautomeric form, for example thiazolin-4,5-dion-2-yl, 3-oxo-3H-1,2,4-dithiazolyl or 2-oxo-2H-1,3,4-dithiazolyl.

Examples of benzo-fused 5- or 6-membered heteroaromatic rings are benzofuranyl, benzothienyl, indolyl, benzoxazolyl, benzisoxazo-lyl, benzothiazolyl, benzisothiazolyl, benzopyrazolyl, indazolyl, 1,2,3-benzothiadiazolyl, 2,1,3-benzothiadiazolyl, benzotriazolyl, benzofuroxanyl, quinolinyl, isoquinolinyl, cinnolinyl, quinazolinyl, quinoxalinyl or phthalazinyl. Examples of particularly preferred compounds of the general formula I are compiled in Tables 1 to 5 below.

TABLE 1

Compounds of the structure Ie

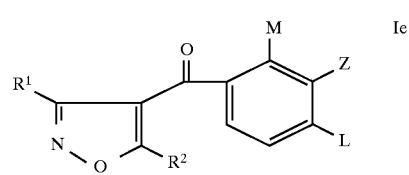

| No. | R$^1$ | R$^2$ | L | M | Z |
|---|---|---|---|---|---|
| 1.1 | H | cyclo-propyl | SO$_2$CH$_3$ | Cl | 2-thienyl |
| 1.2 | H | cyclo-propyl | SO$_2$CH$_3$ | Cl | 3-thienyl |
| 1.3 | H | cyclo-propyl | SO$_2$CH$_3$ | Cl | 2-furyl |
| 1.4 | H | cyclo-propyl | SO$_2$CH$_3$ | Cl | 3-furyl |
| 1.5 | H | cyclo-propyl | SO$_2$CH$_3$ | Cl | 3-methylisoxazol-5-yl |
| 1.6 | H | cyclo-propyl | SO$_2$CH$_3$ | Cl | 5-thiazolyl |
| 1.7 | H | cyclo-propyl | SO$_2$CH$_3$ | Cl | 4-thiazolyl |
| 1.8 | H | cyclo-propyl | SO$_2$CH$_3$ | Cl | 2-thiazolyl |
| 1.9 | H | cyclo-propyl | SO$_2$CH$_3$ | Cl | 3-methyl-isothiazol-5-yl |
| 1.10 | H | cyclo-propyl | SO$_2$CH$_3$ | Cl | 3-isoxazolyl |
| 1.11 | H | cyclo-propyl | SO$_2$CH$_3$ | Cl | 5-phenylthiazol-2-yl |
| 1.12 | H | cyclo-propyl | SO$_2$CH$_3$ | Cl | 2-pyridyl |
| 1.13 | H | cyclo-propyl | SO$_2$CH$_3$ | Cl | 3-pyridyl |
| 1.14 | H | cyclo-propyl | SO$_2$CH$_3$ | Cl | 4-pyridyl |
| 1.15 | H | cyclo-propyl | SO$_2$CH$_3$ | Cl | 1-methyl-2-pyrrolyl |
| 1.16 | H | cyclo-propyl | SO$_2$CH$_3$ | Cl | 1-methyl-1,2,4-triazol-5-yl |
| 1.17 | H | cyclo-propyl | SO$_2$CH$_3$ | Cl | 2-benzothiazolyl |

TABLE 1-continued

Compounds of the structure Ie

| No. | R¹ | R² | L | M | Z |
|---|---|---|---|---|---|
| 1.18 | H | cyclopropyl | SO$_2$CH$_3$ | Cl | 2-quinolinyl |
| 1.19 | H | cyclopropyl | SO$_2$CH$_3$ | Cl | 1-methylbenzimidazol-2-yl |
| 1.20 | H | cyclopropyl | SO$_2$CH$_3$ | Cl | 2-oxazolyl |
| 1.21 | H | cyclopropyl | SO$_2$CH$_3$ | Cl | 1-phenylpyrazol-5-yl |
| 1.22 | H | cyclopropyl | SO$_2$CH$_3$ | Cl | 1-methylpyrazol-3-yl |
| 1.23 | H | cyclopropyl | SO$_2$CH$_3$ | Cl | 1-methylpyrazol-5-yl |
| 1.24 | H | cyclopropyl | SO$_2$CH$_3$ | Cl | 1,3-dimethylpyrazol-3-yl |
| 1.25 | H | cyclopropyl | SO$_2$CH$_3$ | Cl | 1-phenylpyrazol-3-yl |
| 1.26 | H | cyclopropyl | SO$_2$CH$_3$ | Cl | 1,4-dimethylpyrazol-5-yl |
| 1.27 | H | cyclopropyl | SO$_2$CH$_3$ | Cl | 1,3-dimethylpyrazol-4-yl |
| 1.28 | H | cyclopropyl | SO$_2$CH$_3$ | Cl | 1,5-dimethylpyrazol-4-yl |
| 1.29 | H | cyclopropyl | SO$_2$CH$_3$ | Cl | 1-methylpyrazol-4-yl |
| 1.30 | H | cyclopropyl | SO$_2$CH$_3$ | Cl | 1,3-dimethylpyrazol-5-yl |
| 1.31 | H | cyclopropyl | SO$_2$CH$_3$ | Cl | 4-methyloxazol-2-yl |
| 1.32 | H | cyclopropyl | SO$_2$CH$_3$ | Cl | 5-methylthiothiazol-2-yl |
| 1.33 | H | cyclopropyl | SO$_2$CH$_3$ | Cl | 4-methoxy-1-methyl-pyrazol-5-yl |
| 1.34 | H | cyclopropyl | SO$_2$CH$_3$ | Cl | 3-cyclopropyl-isoxazol-5-yl |
| 1.35 | H | cyclopropyl | SO$_2$CH$_3$ | Cl | 3-Isopropyl-isoxazol-5-yl |
| 1.36 | H | cyclopropyl | SO$_2$CH$_3$ | Cl | (3-methylphenyl)-thiazol-2-yl |
| 1.37 | H | cyclopropyl | SO$_2$CH$_3$ | Cl | 5-methylthiazol-2-yl |
| 1.38 | H | cyclopropyl | SO$_2$CH$_3$ | Cl | 4-bromo-2-thienyl |
| 1.39 | H | cyclopropyl | SO$_2$CH$_3$ | Cl | 5-methyl-2-thienyl |
| 1.40 | H | cyclopropyl | SO$_2$CH$_3$ | Cl | 4-methyl-2-thienyl |
| 1.41 | H | cyclopropyl | SO$_2$CH$_3$ | Cl | 4-methylthiazol-2-yl |
| 1.42 | H | cyclopropyl | SO$_2$CH$_3$ | Cl | 4-chlorothiazol-2-yl |
| 1.43 | H | cyclopropyl | SO$_2$CH$_3$ | Cl | 4,5-dimethylthiazol-2-yl |
| 1.44 | H | cyclopropyl | SO$_2$CH$_3$ | Cl | 4-phenylthiazol-2-yl |
| 1.45 | H | cyclopropyl | SO$_2$CH$_3$ | Cl | 2-methoxythiazol-5-yl |
| 1.46 | H | cyclopropyl | SO$_2$CH$_3$ | Cl | 4-methyl-2-pyridyl |
| 1.47 | H | cyclopropyl | SO$_2$CH$_3$ | Cl | 6-(2-methoxyethyl)-2-pyridyl |
| 1.48 | H | cyclopropyl | SO$_2$CH$_3$ | Cl | 6-methylthio-2-pyridyl |
| 1.49 | H | cyclopropyl | SO$_2$CH$_3$ | Cl | 6-methoxy-3-pyridyl |
| 1.50 | H | cyclopropyl | SO$_2$CH$_3$ | Cl | 6-methoxy-2-pyridyl |
| 1.51 | H | cyclopropyl | SO$_2$CH$_3$ | Cl | 6-methyl-2-pyridyl |
| 1.52 | H | cyclopropyl | SO$_2$CH$_3$ | Cl | 6-(2,2,2-trifluoroethoxy)-2-pyridyl |
| 1.53 | H | cyclopropyl | SO$_2$CH$_3$ | Cl | 6-(2,2,2-trifluoroethoxy)-3-pyridyl |
| 1.54 | H | cyclopropyl | SO$_2$CH$_3$ | Cl | 5-pyrimidinyl |
| 1.55 | H | cyclopropyl | SO$_2$CH$_3$ | Cl | 6-dimethylamino-3-pyridyl |
| 1.56 | H | cyclopropyl | SO$_2$CH$_3$ | Cl | 1,2,4-thiadiazol-5-yl |
| 1.57 | H | cyclopropyl | SO$_2$CH$_3$ | Cl | 3-ethoxycarbonyl-1-methylpyrazol-5-yl |
| 1.58 | H | cyclopropyl | SO$_2$CH$_3$ | Cl | 2-methylthiopyrimidin-5-yl |
| 1.59 | H | cyclopropyl | SO$_2$CH$_3$ | Cl | 2-pyrimidinyl |
| 1.60 | H | cyclopropyl | SO$_2$CH$_3$ | Cl | 2-methylthiopyrimidin-4-yl |
| 1.61 | H | cyclopropyl | SO$_2$CH$_3$ | Cl | 5-methylthio-1,3,4-thiadiazol-2-yl |
| 1.62 | H | cyclopropyl | SO$_2$CH$_3$ | Cl | 5-methoxy-1,3,4-thiadiazol-2-yl |
| 1.63 | H | cyclopropyl | SO$_2$CH$_3$ | Cl | 4,5-dihydrothiazol-2-yl |
| 1.64 | H | cyclopropyl | SO$_2$CH$_3$ | Cl | 5-methyloxazol-2-yl |
| 1.65 | H | cyclopropyl | SO$_2$CH$_3$ | Cl | 5-phenyloxazol-2-yl |
| 1.66 | H | cyclopropyl | SO$_2$CH$_3$ | Cl | 2-methyloxazol-5-yl |
| 1.67 | H | cyclopropyl | SO$_2$CH$_3$ | Cl | 2-phenyloxazol-5-yl |
| 1.68 | H | cyclopropyl | SO$_2$CH$_3$ | Cl | 2-methyl-1,3,4-oxadiazol-5-yl |
| 1.69 | H | cyclopropyl | SO$_2$CH$_3$ | Cl | 2-phenyl-1,3,4-oxadiazol-5-yl |
| 1.70 | H | cyclopropyl | SO$_2$CH$_3$ | Cl | 5-trifluoromethyl-1,2,4-oxadiazol-3-yl |
| 1.71 | H | cyclopropyl | SO$_2$CH$_3$ | Cl | 5-methyl-1,2,4-oxadiazol-3-yl |
| 1.72 | H | cyclopropyl | SO$_2$CH$_3$ | Cl | 5-phenyl-1,2,4-oxadiazol-3-yl |
| 1.73 | H | cyclopropyl | SO$_2$CH$_3$ | Cl | 5-phenyl-isoxazol-3-yl |
| 1.74 | H | cyclopropyl | SO$_2$CH$_3$ | Cl | 1-(4-chlorophenyl)-1,2,4-triazol-2-yl |
| 1.75 | H | cyclopropyl | SO$_2$CH$_3$ | Cl | 5-cyano-4,5-dihydro-isoxazol-3-yl |
| 1.76 | H | cyclopropyl | SO$_2$CH$_3$ | Cl | 5,6-dihydro-4H-1,3-thiazin-2-yl |
| 1.77 | H | cyclopropyl | SO$_2$CH$_3$ | Cl | 1,3-dithiolan-2-yl |
| 1.78 | H | cyclopropyl | SO$_2$CH$_3$ | Cl | 1,3-dioxolan-2yl |
| 1.79 | H | cyclopropyl | SO$_2$CH$_3$ | Cl | 1,3-dithian-2-yl |
| 1.80 | H | cyclopropyl | SO$_2$CH$_3$ | Cl | 1,3-dioxan-2-yl |
| 1.81 | H | cyclopropyl | SO$_2$CH$_3$ | Cl | 1,3-oxathiolan-2-yl |
| 1.82 | H | cyclopropyl | SO$_2$CH$_3$ | Cl | 1,2,4-triazol-1-yl |
| 1.83 | H | cyclopropyl | SO$_2$CH$_3$ | Cl | 3-methyl-1,2,4-thiadiazol-5-yl |

TABLE 1-continued

Compounds of the structure Ie

R¹—[isoxazole]—C(=O)—[phenyl with M, Z, L substituents], R² on isoxazole  Ie

| No. | R¹ | R² | L | M | Z |
|---|---|---|---|---|---|
| 1.84 | H | cyclopropyl | SO₂CH₃ | Cl | 1,2,4-thiadiazol-5-yl |
| 1.85 | H | cyclopropyl | SO₂CH₃ | Cl | thiazolin-4,5-dion-2-yl |
| 1.86 | H | cyclopropyl | SO₂CH₃ | Cl | 3-oxo-3-H-1,2,4-dithiazol-5-yl |
| 1.87 | H | cyclopropyl | SO₂CH₃ | Cl | 2-oxo-2-H-1,3,4-dithiazol-5-yl |
| 1.88 | COOMe | cyclopropyl | SO₂CH₃ | Cl | 3-thienyl |
| 1.89 | COOMe | cyclopropyl | SO₂CH₃ | Cl | 2-furyl |
| 1.90 | COOMe | cyclopropyl | SO₂CH₃ | Cl | 3-furyl |
| 1.91 | COOMe | cyclopropyl | SO₂CH₃ | Cl | 3-methyl-isoxazol-5-yl |
| 1.92 | COOMe | cyclopropyl | SO₂CH₃ | Cl | 5-thiazolyl |
| 1.93 | COOMe | cyclopropyl | SO₂CH₃ | Cl | 4-thiazolyl |
| 1.94 | COOMe | cyclopropyl | SO₂CH₃ | Cl | 2-thiazolyl |
| 1.95 | COOMe | cyclopropyl | SO₂CH₃ | Cl | 3-isoxazolyl |
| 1.96 | COOMe | cyclopropyl | SO₂CH₃ | Cl | 2-pyridyl |
| 1.97 | COOMe | cyclopropyl | SO₂CH₃ | Cl | 3-pyridyl |
| 1.98 | COOMe | cyclopropyl | SO₂CH₃ | Cl | 4-pyridyl |
| 1.99 | COOMe | cyclopropyl | SO₂CH₃ | Cl | 2-benzothiazolyl |
| 1.100 | COOMe | cyclopropyl | SO₂CH₃ | Cl | 2-quinolinyl |
| 1.101 | COOMe | cyclopropyl | SO₂CH₃ | Cl | 4-methyloxazol-2-yl |
| 1.102 | COOMe | cyclopropyl | SO₂CH₃ | Cl | 5-pyrimidinyl |
| 1.103 | Me | cyclopropyl | SO₂CH₃ | Cl | 3-thienyl |
| 1.104 | Me | cyclopropyl | SO₂CH₃ | Cl | 2-furyl |
| 1.105 | Me | cyclopropyl | SO₂CH₃ | Cl | 3-furyl |
| 1.106 | Me | cyclopropyl | SO₂CH₃ | Cl | 3-methylisoxazol-5-yl |
| 1.107 | Me | cyclopropyl | SO₂CH₃ | Cl | 5-thiazolyl |
| 1.108 | Me | cyclopropyl | SO₂CH₃ | Cl | 4-thiazolyl |
| 1.109 | Me | cyclopropyl | SO₂CH₃ | Cl | 2-thiazolyl |
| 1.110 | Me | cyclopropyl | SO₂CH₃ | Cl | 3-isoxazolyl |
| 1.111 | Me | cyclopropyl | SO₂CH₃ | Cl | 2-pyridyl |
| 1.112 | Me | cyclopropyl | SO₂CH₃ | Cl | 3-pyridyl |
| 1.113 | Me | cyclopropyl | SO₂CH₃ | Cl | 4-pyridyl |
| 1.114 | Me | cyclopropyl | SO₂CH₃ | Cl | 2-benzothiazolyl |
| 1.115 | Me | cyclopropyl | SO₂CH₃ | Cl | 2-quinolinyl |
| 1.116 | Me | cyclopropyl | SO₂CH₃ | Cl | 4-methyloxazol-2-yl |
| 1.117 | Me | cyclopropyl | SO₂CH₃ | Cl | 5-pyrimidinyl |
| 1.118 | H | tert-butyl | SO₂CH₃ | Cl | 3-thienyl |
| 1.119 | H | tert-butyl | SO₂CH₃ | Cl | 2-furyl |
| 1.120 | H | tert-butyl | SO₂CH₃ | Cl | 3-furyl |
| 1.121 | H | tert-butyl | SO₂CH₃ | Cl | 3-methylisoxazol-5-yl |
| 1.122 | H | tert-butyl | SO₂CH₃ | Cl | 5-thiazolyl |
| 1.123 | H | tert-butyl | SO₂CH₃ | Cl | 4-thiazolyl |
| 1.124 | H | tert-butyl | SO₂CH₃ | Cl | 2-thiazolyl |
| 1.125 | H | tert-butyl | SO₂CH₃ | Cl | 3-isoxazolyl |
| 1.126 | H | tert-butyl | SO₂CH₃ | Cl | 2-pyridyl |
| 1.127 | H | tert-butyl | SO₂CH₃ | Cl | 3-pyridyl |
| 1.128 | H | tert-butyl | SO₂CH₃ | Cl | 4-pyridyl |
| 1.129 | H | tert-butyl | SO₂CH₃ | Cl | 2-benzothiazolyl |
| 1.130 | H | tert-butyl | SO₂CH₃ | Cl | 2-quinolinyl |
| 1.131 | H | tert-butyl | SO₂CH₃ | Cl | 4-methyloxazol-2-yl |
| 1.132 | H | tert-butyl | SO₂CH₃ | Cl | 5-pyrimidinyl |
| 1.133 | H | cyclopropyl | SO₂CH₃ | Me | 3-thienyl |
| 1.134 | H | cyclopropyl | SO₂CH₃ | Me | 2-furyl |
| 1.135 | H | cyclopropyl | SO₂CH₃ | Me | 3-furyl |
| 1.136 | H | cyclopropyl | SO₂CH₃ | Me | 3-methylisoxazol-5-yl |
| 1.137 | H | cyclopropyl | SO₂CH₃ | Me | 5-thiazolyl |
| 1.138 | H | cyclopropyl | SO₂CH₃ | Me | 4-thiazolyl |
| 1.139 | H | cyclopropyl | SO₂CH₃ | Me | 2-thiazolyl |
| 1.140 | H | cyclopropyl | SO₂CH₃ | Me | 3-isoxazolyl |
| 1.141 | H | cyclopropyl | SO₂CH₃ | Me | 2-pyridyl |
| 1.142 | H | cyclopropyl | SO₂CH₃ | Me | 3-pyridyl |
| 1.143 | H | cyclopropyl | SO₂CH₃ | Me | 4-pyridyl |
| 1.144 | H | cyclopropyl | SO₂CH₃ | Me | 2-benzothiazolyl |
| 1.145 | H | cyclopropyl | SO₂CH₃ | Me | 2-quinolinyl |
| 1.146 | H | cyclopropyl | SO₂CH₃ | Me | 4-methyloxazol-2-yl |
| 1.147 | H | cyclopropyl | SO₂CH₃ | Me | 5-pyrimidinyl |

The compounds I and their agriculturally useful salts are suitable as herbicides, both in the form of isomer mixtures and pure isomers. The herbicidal compositions comprising I control vegetation on non-cultivated land very effectively, particularly at high application rates. They act against broad-leaved weeds and grass weeds in crops such as wheat, rice, maize, soya beans and cotton without significantly damaging the crop plants. This effect occurs particularly at low application rates.

Taking into consideration the versatility of the application methods, the compounds I, or compositions comprising them, can additionally be used in a large number of crop plants for eliminating undesirable plants. Suitable crops are, for example, the following:

*Allium cepa, Ananas comosus, Arachis hypogaea, Asparagus officinalis, Beta vulgaris* ssp. *altissima, Beta*

*vulgaris ssp. rapa, Brassica napus var. napus, Brassica napus var. napobrassica, Brassica rapa var. silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossyplum hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus spp., Manihot esculenta, Medicago sativa, Musa spp., Nicotiana tabacum (N. rustica), Olea europaea, Oryza sativa, Phaseolus lunatus, Phaseolus vulgaris, Picea abies, Pinus spp., Pisum sativum, Prunus avium, Prunus persica, Pyrus communis, Ribes sylvestre, Ricinus communis, Saccharum officinarum, Secale cereale, Solanum tuberosum, Sorghum bicolor (s. vulgare), Theobroma cacao, Trifolium pratense, Triticum aestivum, Triticum durum, Vicia faba, Vitis vinifera, Zea mays.*

In addition, the compounds I can also be used in crops which are tolerant against the action of herbicides due to breeding, including genetic engineering methods. The herbicidal compositions or the active ingredients can be applied pre- or post-emergence. If the active ingredients are less well tolerated by certain crop plants, application techniques may be used in which the herbicidal compositions are sprayed, with the aid of the spraying equipment, in such a way that they come into as little contact as possible with the leaves of the sensitive crop plants, while reaching the leaves of undesirable plants growing underneath, or the naked soil surface (post-directed, lay-by).

The compounds I, or the herbicidal compositions comprising them, can be applied, for example, in the form of directly sprayable aqueous solutions, powders, suspensions, also highly concentrated aqueous oily or other suspensions or dispersions, emulsions, oil dispersions, pastes, dusts, spreading materials or granules, by means of spraying, atomizing, dusting, scattering or pouring. The use forms depend on the intended purposes; in any case, they should guarantee the finest possible distribution of the active ingredients according to the invention. Suitable inert additives are mineral oil fractions of medium to high boiling point, such as kerosene or diesel oil, furthermore coal tar oils and oils of vegetable or animal origin, aliphatic, cyclic and aromatic hydrocarbons, eg. paraffin, tetrahydronaphthalene, alkylated naphthalenes or their derivatives, alkylated benzenes or their derivatives, methanol, ethanol, propanol, butanol, cyclohexanol, cyclohexanone or strongly polar solvents, such as N-methyl-pyrrolidone or water.

Aqueous use forms can be prepared from emulsion concentrates, suspensions, pastes, wettable powders or water-dispersible granules by adding water. To prepare emulsions, pastes or oil dispersions, the substances, either as such or dissolved in an oil or solvent, can be homogenized in water by means of a wetting agent, tackifier, dispersant or emulsifier. Alternatively, it is also possible to prepare concentrates comprising active ingredient, wetting agent, tackifier, dispersant or emulsifier and, if desired, solvent or oil, and which are suitable for dilution with water.

Suitable surfactants (adjuvants) are the alkali metal salts, alkaline earth metal salts and ammonium salts of aromatic sulfonic acids, eg. ligno-, phenol-, naphthalene- and dibutylnaphthalenesulfonic acid, or of fatty acids, alkyl- and alkylarylsulfonates, alkyl, lauryl ether and fatty alcohol sulfates, and salts of sulfated hexa-, hepta- and octadecanols, and also of fatty alcohol glycol ether, condensation products of sulfonated naphthalene and its derivatives with formaldehyde, condensation products of naphthalene or of the naphthalenesulfonic acids with phenol and formaldehyde, polyoxyethylene octylphenol ether, ethoxylated isooctyl-, octyl or nonylphenol, alkylphenyl polyglycol ether, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, spreading materials and dusts can be prepared by mixing or grinding the active ingredients together with a solid carrier.

Granules, eg. coated granules, impregnated granules and homogeneous granules, can be prepared by binding the active ingredients to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground polymers, fertilizers, such as ammonium sulfate, ammonium phosphate, ammonium nitrate, ureas, and products of vegetable origin, such as cereal meal, tree bark meal, wood meal and nutshell meal, cellulose powder, or other solid carriers.

The concentrations of the active ingredients I in the ready-to-use preparations can be varied within wide ranges. In general, the formulations comprise from 0.001 to 98% by weight, preferably 0.01 to 95% by weight, of active ingredient. The active ingredients are employed in a purity from 90% to 100%, preferably 95% to 100% (in accordance with NMR spectrum).

The compounds I according to the invention can be formulated for example as follows:

I 20 parts by weight of Compound No. 1.8 are dissolved in a mixture composed of 80 parts by weight of alkylated benzene, 10 parts by weight of the adduct of 8 to 10 mol of ethylene oxide to 1 mol of the monoamide derived from oleic acid and ethanol, 5 parts by weight of the calcium salt of dodecylbenzenesulfonic acid and 5 parts by weight of the adduct of 40 mol of ethylene oxide to 1 mol of castor oil. Pouring the solution into 100 000 parts by weight of water and finely distributing it therein gives an aqueous dispersion comprising 0.02% by weight of the active ingredient.

II 20 parts by weight of Compound No. 1.8 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100 000 parts by weight of water and finely distributing it therein gives an aqueous dispersion comprising 0.02% by weight of the active ingredient.

III 20 parts by weight of the active ingredient of No. 1.8 are dissolved in a mixture composed of 25 parts by weight of cyclohexanone, 65 parts by weight of a mineral oil fraction of boiling point 210° to 280° C. and 10 parts by weight of the adduct of 40 mol of ethylene oxide to 1 mol of castor oil. Pouring the solution into 100 000 parts by weight of water and finely distributing it therein gives an aqueous dispersion comprising 0.02% by weight of the active ingredient.

IV 20 parts by weight of the active ingredient of No. 1.8 are mixed thoroughly with 3 parts by weight of the sodium salt of diisobutylnaphthalenesulfonic acid, 17 parts by weight of the sodium salt of a lignosulfonic acid from a sulfite waste liquor and 60 parts by weight of pulverulent silica gel, and the mixture is ground in a hammer mill. Finely distributing the mixture in 20 000 parts of water gives a spray mixture comprising 0.1% by weight of the active ingredient.

V 3 parts by weight of the active ingredient of No. 1.8 are mixed with 97 parts by weight of finely divided kaolin. This gives a dust comprising 3% by weight of the active ingredient.

VI 20 parts by weight of the active ingredient of No. 1.8 are mixed intimately with 2 parts by weight of the calcium salt of dodecylbenzenesulfonic acid, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII 1 part by weight of Compound No. 1.8 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII 1 part by weight of Compound No. 1.8 is dissolved in a mixture composed of 80 parts by weight of cyclohexanone and 20 parts by weight of Emulphor EL. This gives a stable emulsion concentrate.

To widen the spectrum of action and to achieve synergistic effects, the isoxazolylbenzoyl derivatives I may be mixed with a large number of representatives of other groups of herbicidal or growth-regulating active ingredients and then applied concomitantly. Suitable components for mixtures are diazines, 4H-3,1-benzoxazine derivatives, benzothiadiazinones, 2, 6-dinitroani-lines, N-phenylcarbamates, thiocarbamates, halocarboxylic acids, triazines, amides, ureas, diphenyl ethers, triazinones, uracils, benzofuran derivatives, cyclohexane-1,3-dione derivatives having attached to them in the 2-position for example a carboxyl or carbimino group, or quinolinecarboxylic acid derivatives, imidazolinones, sulfonamides, sulfonylureas, aryloxy- or heteroaryloxyphenoxypropionic acids and their salts, esters and amides, and others.

It may furthermore be advantageous to apply the compounds I, alone or in combination with other herbicides, together with further crop protection agents, for example with pesticides or agents for controlling phytopathogenic fungi or bacteria. Also interesting is the miscibility with mineral salt solutions, which are employed for treating nutrient and trace element deficiencies. Non-phytotoxic oils and oil concentrates may also be added.

Depending on the intended purpose, the season, the target plants and the growth stage, the application rates of active ingredient are from 0.001 to 3.0, preferably 0.01 to 1.0, kg of active ingredient (a.i.) per ha.

EXAMPLES

The herbicidal action of the isoxazolylbenzoyl derivatives of the formula I was demonstrated by greenhouse experiments:

The culture containers used were plastic flowerpots containing loamy sand with approximately 3.0% of humus as the substrate. The seeds of the test plants were sown separately for each species.

In the case of the pre-emergence treatment, the active ingredients, which were suspended or emulsified in water, were applied directly after sowing by means of finely distributing nozzles. The containers were irrigated gently to promote germination and growth and subsequently covered with translucent plastic hoods until the plants had rooted. This cover results in uniform germination of the test plants, unless germination was adversely affected by the active ingredients.

For the post-emergence treatment, the test plants were first grown to a plant height of 3 to 15 cm, depending on the growth form, and only then treated with the active ingredients which were suspended or emulsified in water. The test plants were either sown directly and grown in the same containers, or grown separately as seedlings and transplanted to the test containers a few days prior to treatment.

The plants were kept at from 10°–25° C. or 20°–35° C., depending on the species. The test period extended to 2 to 4 weeks. During this time, the plants were looked after, and their response to the individual treatments was evaluated.

Evaluation was carried out using a scale from 0 to 100. 100 means no plant emergence or complete destruction of at least the aerial parts, and 0 means no damage or normal growth.

Preparation examples

A) Preparation of the starting materials

1. Methyl 2-chloro-3-formyl-4-methylsulfonylbenzoate a. A solution of 157 g (2 mol) of acetyl chloride in 420 ml of 1,2-dichloroethane was added dropwise at 15°–20° C. to a suspension of 286 g (2.14 mol) of aluminum trichloride in 420 ml of 1,2-dichloroethane. A solution of 346 g (2 mol) of 2-chloro-6-methylthiotoluene in 1 l of 1,2-dichloroethane was subsequently added dropwise. After stirring had been continued for 12 hours, the reaction mixture was poured into a mixture of 3 l of ice and 1 l of concentrated HCl. The mixture was extracted using methylene chloride, and the organic phase was washed with water, dried using sodium sulfate and concentrated. The residue was distilled in vacuo.

This gave 256 g (60% of theory) of 2-chloro-3-methyl-4-methylthioacetophenone, m.p.: 46° C.

b. 163 g (0.76 mol) of 2-chloro-3-methyl-4-methylthioacetophenone were dissolved in 1.5 l of glacial acetic acid, 18.6 g of sodium tungstate were added, and 173.3 g of 30% strength hydrogen peroxide solution was added dropwise with cooling. Stirring was continued for 2 days and the mixture was subsequently diluted with water. The solid which had precipitated was filtered off, washed with water and dried.

This gave 164 g (88% of theory) of 2-chloro-3-methyl-4-methylsulfonylacetophenone, m.p.: 110°–111° C.

c. 82 g (0.33 mol) of 2-chloro-3-methyl-4-methylsulfonylacetophenone were dissolved in 700 ml of dioxane, and 1 l of a 12.5% strength sodium hypochlorite solution was added at room temperature. Stirring was subsequently continued at 80° C. for 1 hour. After cooling, two phases formed, of which the bottom phase was diluted with water and rendered weakly acidic. The solid which had precipitated was washed with water and dried.

This gave 60 g (73% of theory) of 2-chloro-3-methyl-4-methylsulfonylbenzoic acid, m.p.: 230°–231° C.

d. 100 g (0.4 mol) of 2-chloro-3-methyl-4-methylsulfonyl-benzoic acid were dissolved in 1 l of methanol, and HCl was passed in for 5 hours at reflux temperature. The mixture was subsequently concentrated.

This gave 88.5 g (84% of theory) of methyl 2-chloro-3-methyl-4-methylsulfonylbenzoate, m.p.: 107°–108°C.

e. 82 g (0.31 mol) of methyl 2-chloro-3-methyl-4-methylsulfonylbenzoate were dissolved in 2 l of tetrachloromethane, and 56 g (0.31 mol) of N-bromosuccinimide were added, a little at a time, with exposure to light. The reaction mixture was filtered, the filtrate concentrated and the residue taken up in 200 ml of methyl tert-butyl ether. The solution was treated with petroleum ether and the solid which had precipitated was filtered off with suction and dried.

This gave 74.5 g (70% of theory) of methyl 3-bromomethyl-2-chloro-4-methylsulfonylbenzoate, m.p. 74°–75° C.

f. A solution of 41 g (0.12 mol) of 3-bromomethyl-2-chloro-4-methylsulfonylbenzoate in 250 ml of acetonitrile was treated with 42.1 g (0.36 mol) of N-methylmorpholine N-oxide. Stirring of the batch was continued at room temperature for 12 hours, and the batch was subsequently concentrated and the residue taken up in ethyl acetate.

The solution was extracted with water, dried using sodium sulfate and concentrated.

This gave 31.2 g (94% of theory) of methyl 2-chloro-3-formyl-4-methylsulfonylbenzoate, m.p.: 98°–105° C.

2. Methyl 2-chloro-4-methylsulfonyl-3-(trifluoromethylsulfonyl)-oxybenzoate a. 101 g (0.41 mol) of 2-chloro-3-hydroxy-4-methylsulfonylbenzoic acid were dissolved in 1.3 l of methanol, and HCl was passed in for 4 hours under reflux conditions. The solution was concentrated, the residue taken up in dichloromethane and the mixture extracted using $K_2CO_3$ solution. The aqueous phase was brought to pH 7 using dilute hydrochloric acid and washed using dichloromethane. The mixture was subsequently brought to pH 1 and the product extracted using dichloromethane.

This gave 76.2 g (71% of theory) of methyl 2-chloro-3-hydroxy-4-methylsulfonylbenzoate.

b. A solution of 76 g (0.29 mol) of 2-chloro-3-hydroxy-4-methylsulfonylbenzoate and 68 g of pyridine in 700 ml of dichloromethane was treated at −20° C. with 89 g (0.32 mol) of trifluoromethanesulfonic anhydride. Stirring of the solution was continued at room temperature for 12 hours, and the mixture was diluted with dichloromethane and extracted using water. The organic phase was dried over magnesium sulfate and concentrated.

This gave 94 g (82% of theory) of methyl 2-chloro-4-methylsulfonyl-3-(trifluoromethylsulfonyl)oxybenzoate, m.p.: 69° C.

B) Preparation of the intermediates

1. Methyl 3-(3-isopropylisoxazol-5-yl)-4-methylsulfonylbenzoate a. 30 g (102 mmol) of methyl 3-bromo-4-methylsulfonylbenzoate, 90 mg of palladium dichloride and 240 mg of triphenylphosphine in 200 ml of diethylamine and 60 ml of dimethylformamide were treated with 10 g (102 mmol) of (trimethylsilyl)acetylene and 180 mg of copper(I) iodide, and the mixture was stirred at 40° C. for 4.5 hours. Stirring was subsequently continued at room temperature for 12 hours. The reaction mixture was filtered, the filtrate was concentrated and the residue was chromatographed over silica gel using toluene as the eluent.

This gave 17.3 g (55% of theory) of methyl 4-methylsulfonyl-3-(trimethylsilyl)ethynylbenzoate as an oil.

b. 25 g of methyl 4-methylsulfonyl-3-(trimethylsilyl) ethynylbenzoate together with 100 ml of methanol and 0.9 g of potassium carbonate are stirred at room temperature for 18 hours. The solid was subsequently removed by filtration with suction and the filtrate was concentrated and extracted using ethyl acetate/water. The organic phase was dried over sodium sulfate and concentrated.

This gave 15 g (79% of theory) of methyl 4-methylsulfonyl-3-ethynylbenzoate, m.p.: 95°–98° C.

c. 13.5g (57 mmol) of methyl 4-methylsulfonyl-3-ethynylbenzoate were dissolved in 50 ml of dichloromethane, 5.2 g (60 mmol) of isobutyraldehyde oxime were added, and 41 g of a 12.5% strength sodium hypochlorite solution were added dropwise. Stirring was subsequently continued at room temperature for 24 hours. The reaction batch was subsequently extracted using dichloromethane/water, the organic phase was concentrated, and the residue was chromatographed over silica gel using toluene/ethyl acetate as the eluent.

This gave 8.8 g (48% of theory) of methyl 3-(3-isopropylisoxazol-5-yl)-4-methylsulfonylbenzoate, m.p.: 102°–104° C.

2. Methyl 2-chloro-3-(isoxazol-3-yl)-4-methylsulfonylbenzoate a. 15 g (54 mmol) of methyl 2-chloro-3-formyl-4-methylsulfonylbenzoate (Ex. A.1.) and 4.2 g (60 mmol) of hydroxylamine hydrochloride were stirred with 300 ml of methanol, and a solution of 3.18 g (30 mmol) of sodium carbonate in 80 ml of water was added dropwise. The reaction miture was stirred overnight at room temperature, the methanol was subsequently distilled off, and the batch was extracted using ether/water. The ether phase was dried using sodium sulfate and concentrated.

This gave 14.4 g (91% of theory) of methyl 2-chloro-3-hydroxyiminomethyl-4-methylsulfonylbenzoate, m.p.: 126°–128° C.

b. 5.3 g (18 mmol) of methyl 2-chloro-3-hydroxyiminomethyl-4-methylsulfonylbenzoate were dissolved in 50 ml of dichloromethane, and acetylene was passed in for 30 minutes at 0°–5° C. Subsequently, a spatula-tip full of sodium acetate was added, and 15 ml of a 10% strength sodium hypochlorite solution was added dropwise at 10° C. while passing in more acetylene. After the addition had ended, acetylene was passed in at 10° C. for a further 15 minutes, and stirring was subsequently continued for 12 hours. The phases were then separated, and the organic phase was washed with water, dried using sodium sulfate and concentrated.

This gave 4.8 g (84% of theory) of methyl 2-chloro-3-(isoxazol-3-yl)-4-methylsulfonylbenzoate, m.p.: 145°–147° C.

3. Methyl 2-chloro-3-(thiazol-3-yl)-4-methylsulfonylbenzoate 33 g (88 mol) of 2-(tributylstannyl)thiazole, 17.5 g (44 mmol) of methyl 2-chloro-4-methylsulfonyl-3-(trifluoromethylsulfonyl)oxybenzoate (Ex. A.2.), 5.8 g of lithium chloride, 1 g of tetrakis(triphenylphosphine) palladium(0), a spatula-tip full of 2,6-di-tert-butyl-4-methylphenol and 200 ml of 1,4-dioxane were stirred in an autoclave at 140° C. for 3 hours under inherent pressure. After cooling, the reaction mixture is filtered through a silica gel layer, washed with methyl tert-butyl ether and concentrated. The residue is chromatographed over silica gel using toluene/ethyl acetate as the eluent.

This gave 9.1 g (62.6% of theory) of methyl 2-chloro-3-(thiazol-2-yl)-4-methylsulfonylbenzoate, m.p.: 135°–138° C.

4. Methyl 2-chloro-3-(oxazol-5-yl)-4-methylsulfonylbenzoate 25 g (0.09 mol) of methyl 2-chloro-3-formyl-4-methylsulfonylbenzoate (Ex. A.1.), 17.6 g (0.09 mol) of tosylmethylene isocyanide and 6.2 g (0.045 mol) of finely pulverulent potassium carbonate are stirred together with 450 ml of methanol at reflux temperature for 5 hours. The solvent was subsequently stripped off, the residue was taken up in ethyl acetate, and the mixture was extracted with water. The ethyl acetate phase was dried using sodium sulfate and concentrated.

This gave 24.7 g (87% of theory) of methyl 2-chloro-3-(oxa5 zol-5-yl)-4-methylsulfonylbenzoate, $^1$H NMR (CDCl$_3$) δ: 8.24 (d,1H), 8.15 (s,1H), 8.01 (d,1H), 7.40 (s,1H), 4.0 (s,3H), 2.96 (s,3H)

The intermediates listed in the table below are obtained in a similar manner:

TABLE 2

IIIa structure: T-C(=O)-phenyl with substituents M, Z, L

| No. | T | L | M | Z | Physical data M.p. [°C.] or $^1$H NMR |
|---|---|---|---|---|---|
| 2.1 | methoxy | —SO$_2$Me | Cl | 3-furyl | $^1$H NMR (CDCl$_3$) δ: 8.24(d, 1H), 7.82(d, 1H), 7.64(m, 2H), 6.55(s, 1H) 3.99(s, 3H), 2.80(s, 3H) |
| 2.2 | methoxy | —SO$_2$Me | H | 2-thiazolyl | 95–98 |
| 2.3 | ethoxy | —SO$_2$Et | Cl | 2-thiazolyl | $^1$H NMR (CDCl$_3$) δ: 8.18(d, 1H), 7.97(m, 2H), 7.71(d, 1H), 4.47(q, 2H), 3.36(q, 2H), 1.42(t, 3H), 1.24(t, 3H) |
| 2.4 | OH | —SO$_2$CH$_3$ | Cl | 2-thiazolyl | 288–290 |
| 2.5 | OH | —SO$_2$CH$_3$ | Cl | 2-thienyl | 177–180 |
| 2.6 | OH | —SO$_2$CH$_3$ | CH$_3$ | 2-thienyl | 175–178 |
| 2.7 | OH | —SO$_2$CH$_3$ | CH$_3$ | 2-furyl | 167–171 |
| 2.8 | methoxy | —SO$_2$CH$_3$ | CH$_3$ | 2-thienyl | 91–95 |
| 2.9 | OH | —SO$_2$CH$_3$ | H | 2-furyl | 219–223 |
| 2.10 | methoxy | —SO$_2$CH$_3$ | CH$_3$ | 2-furyl | 103–106 |
| 2.11 | OH | —SO$_2$CH$_3$ | H | 2-thienyl | 222–224 |
| 2.12 | methoxy | —SO$_2$CH$_3$ | Cl | 3-isoxazolyl | $^1$H NMR (CDCl$_3$): 8.62(1H); 8.18(1H); 8.00(1H); 6.58(1H); 3.98(3H); 3.22(3H) |
| 2.13 | Methoxy | —SO$_2$CH$_3$ | Cl | 5-phenyl-oxazol-2-yl | 115–118 |
| 2.14 | methoxy | —SO$_2$CH$_3$ | Cl | 5-oxazolyl | $^1$H NMR (CDCl$_3$): 8.76(1H); 8.22(1H); 8.10(1H); 7.63(1H); 4.04(3H); 3.08(3H) |
| 2.15 | methoxy | —SO$_2$CH$_3$ | Cl | 5-cyclo-propyl-isoxazolyl | $^1$H NMR (CDCl$_3$): 8.20(1H); 7.95(1H); 6.12(1H); 3.98(3H); 3.22(3H); 2.15(1H); 1.03–1.09(4H) |
| 2.16 | methoxy | —SO$_2$CH$_3$ | Cl | 4,5-di-hydroisox-azol-3-yl | $^1$H NMR (CDCl$_3$): 8.12(1H); 7.98(1H); 4.60(2H); 3.98(3H); 3.42(2H); 3.25(3H) |
| 2.17 | methoxy | —SO$_2$CH$_3$ | Cl | 5-methyl-1,2,4-oxa-diazol-3-yl | 102–105 |
| 2.18 | methoxy | —SO$_2$CH$_3$ | Cl | 4,5-di-hydroox-azol-2-yl | $^1$H NMR (CDCl$_3$): 8.08(1H); 7.98(1H); 4.57(2H); 4.12(2H); 3.98(3H); 3.29(3H) |
| 2.19 | OH | —SO$_2$CH$_3$ | Cl | 3-furyl | $^1$H NMR (CDCl$_3$): 8.29(1H); 8.02(1H); 7.67(2H); 6.59(1H); 2.83(3H) |
| 2.20 | methoxy | —SO$_2$CH$_3$ | Cl | 3-thienyl | $^1$H NMR (CDCl$_3$): 8.23(1H); 7.84(1H); 7.49(2H); 7.13(1H); 3.98(3H); 2.62(3H) |
| 2.21 | OH | —SO$_2$CH$_3$ | H | 3-furyl | 200–202 |
| 2.22 | OH | —SO$_2$CH$_3$ | Cl | 5-methyl-4-phenylthia-zol-2-yl | 200–204 | c) Preparation of the end products

1.

a) 8 g (25 mmol) of methyl 2-chloro-4-methylsulfonyl-(3-thiazol-2-yl)-benzoate are dissolved in 50 ml of methanol and the solution is treated with 1.5 g (37 mmol) of NaOH. The solution is stirred for 12 hours at room temperature. The reaction mixture is subsequently concentrated, and the residue is taken up in water and acidified using hydrochloric acid. Pale yellow crystals form upon prolonged stirring. The solid is filtered off with suction and dried.

This gives 6.6 g (86% of theory) of 2-chloro-4-methylsulfonyl-(3-thiazol-2-yl)benzoic acid, m.p.: 288°–290° C.

b. 6 g (19 mmol) of 2-chloro-4-methylsulfonyl-(3-thiazol-2-yl)benzoic acid are dissolved in 60 ml of toluene, the solution is treated with one drop of dimethylformamide, and 3.2 g (27 mmol) of thionyl chloride are added. After refluxing for 4 hours, the reaction mixture is concentrated.

This gives 6.3 g (99% of theory) of 2-chloro-4-methylsulfonyl-(3-thiazol-2-yl)benzoyl chloride, m.p.: 97°–98° C.

c. A suspension of 2.55 g (0.023 mol) of (pulverulent) calcium chloride in 150 ml of acetone is treated in succession with 4.2 g (0.023 mol) of tert-butyl 3-oxo-3-cyclopropylpropionate and 4.65 g (0.046 mol) of triethylamine. After the mixture has been stirred for one hour at room temperature, 7.65 g (0.023 mol) of 2-chloro-4-methylsulfonyl-(3-thiazol-2-yl)benzoyl chloride in 75 ml of acetone are added dropwise. The mixture is stirred for 3 hours at 45° C., and the solvent is subsequently removed in vacuo. The residue is dissolved in ethyl acetate and treated with 1N hydrochloric acid. The ethyl acetate phase is filtered through silica gel and concentrated. The crystalline residue is dissolved in 200 ml of toluene, the solution is treated with 0.7 g of p-toluenesulfonic acid, and the mixture is refluxed for 3 hours. It is cooled, filtered through silica gel and concentrated.

This gives 5.85 g (67% of theory) of 1-[2-chloro-4-methylsulfonyl-(3-thiazol-2-yl)phenyl]-3-cyclopropyl-propane-1,3-dione, m.p.: 146°–147° C.

d. A mixture of 2.4 g (0.006 mol) of 1-[2-chloro-4-methylsulfonyl-(3-thiazol-2-yl)phenyl]-3-cyclopropylpropane-1,3-dione, 0.96 g (0.009 mol) of acetic anhydride and 20 ml of triethyl orthoformate is stirred for 3 hours at 110° C. and subsequently concentrated. The product is purified by column chromatography using toluene/ethyl acetate as the eluent.

This gives 2.4 g (93% of theory) of 1-[2-chloro-4-methylsulfonyl-(3-thiazol-2-yl)phenyl]-3-cyclopropyl-2-hydroxymethylenepropane-1,3-dione, m.p.: 176° C.

e. 2.4 g (0.006 mol) of 1-[2-chloro-4-methylsulfonyl-(3-thiazol-2-yl)phenyl]-3-cyclopropyl-2-hydroxymethylenepropane-1,3-dione together with 0.52 g (0.007 mol) of hydroxylamine hydrochloride are introduced into 60 ml of dichloromethane, and a solution of 4 g of sodium carbonate in 50 ml of water is added dropwise at room temperature. The mixture is stirred at room temperature for 15 hours. The phases are subsequently separated and the organic phase is concentrated. The crude product is purified by column chromatography using toluene/ethyl acetate as the eluent.

This gives 1.2 g (50% of theory) of 4-[2-chloro-4-methylsulfonyl-(3-thiazol-2-yl)benzoyl]-5-cyclopropylisoxazole, m.p.: 153°–155° C.

The compounds listed in the table below are obtained in a similar manner:

TABLE 3

Compounds of the structure Ie

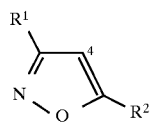

| No. | R¹ | R² | L | M | Z | M.p. [°C.] or ¹H NMR |
|---|---|---|---|---|---|---|
| 3.1 | H | cyclopropyl | SO₂CH₃ | Cl | 3-isoxazolyl | ¹H NMR (CDCl₃) δ: 8.63(1H); 8.28(1H); 8.18(1H); 7.72(1H); 6.63(1H); 3.26(3H); 2.76(1H); 1.25–1.43(4H) |
| 3.2 | H | cyclopropyl | SO₂CH₃ | Cl | 2-thiazolyl | 153–155 |

We claim:

1. An isoxazol-4-ylbenzoyl compound of the formula I

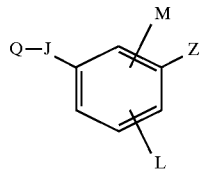

where the substituents have the following meanings:

L and M are hydrogen, $C_1$–$C_6$-alkyl, $C_2$–$C_6$-alkenyl, $C_2$–$C_6$-alkynyl, $C_1$–$C_4$-alkoxy, it being possible for these groups to be unsubstituted or substituted by one to five halogen atoms or $C_1$–$C_4$-alkoxy, or are halogen, cyano, nitro, a group —$(Y)_n$—$S(O)_mR^7$ or —$(Y)_n$—CO—$R^8$, Z is a 5- or 6-membered heterocyclic saturated or unsaturated radical which has one to three heteroatoms selected from a group consisting of oxygen, sulfur or nitrogen and which is unsubstituted or substituted by halogen, cyano, nitro, a group —CO—$R^8$, $C_1$–$C_4$-alkyl, $C_1$–$C_4$-haloalkyl, $C_3$–$C_6$-cycloalkyl, $C_1$–$C_4$-alkoxy, $C_1$–$C_4$-haloalkoxy, $C_1$–$C_4$-alkylthio, $C_1$–$C_4$-haloalkylthio, di-$C_1$–$C_4$-alkylamino, phenyl which is unsubstituted or substituted by halogen, cyano, nitro, $C_1$–$C_4$-alkyl or $C_1$–$C_4$-haloalkyl, or an oxo group which may also exist as a hydroxyl group in the tautomeric form, or which forms a bicyclic system together with a fused phenyl ring which is unsubstituted or substituted by halogen, cyano, nitro, $C_1$–$C_4$-alkyl or $C_1$–$C_4$-haloalkyl, a fused carbocycle or a fused second heterocycle which is unsubstituted or substituted by halogen, cyano, nitro, $C_1$–$C_4$-alkyl, di-$C_1$–$C_4$-alkylamino, $C_1$–$C_4$-alkoxy, $C_1$–$C_4$-haloalkoxy or $C_1$–$C_4$-haloalkyl, Y is O or $NR^9$, n is zero or one, m is zero, one or two, $R^7$ is $C_1$–$C_4$-alkyl, $C_1$–$C_4$-haloalkyl or $NR^9R^{10}$, $R^8$ is $C_1$–$C_4$-alkyl, $C_1$–$C_4$-haloalkyl, $C_1$–$C_4$-alkoxy or $NR^9R^{10}$, $R^9$ is hydrogen or $C_1$–$C_4$-alkyl, $R^{10}$ is $C_1$–$C_4$-alkyl, Q is an isoxazole ring which is linked in the 4-position, of the formula II $$\begin{array}{c} R^1 \\ \diagdown \\ N \\ \diagdown_O \diagup R^2 \end{array} \quad (II)$$

where $R^1$ is hydrogen or —$CO_2R^3$, $R^2$ is hydrogen, $C_1$–$C_4$-alkyl or $C_3$–$C_6$-cycloalkyl, which can be unsubstituted or substituted by one or more halogen atoms or by $C_1$–$C_4$-alkyl and $R^3$ is $C_1$–$C_4$-alkyl, J is a carbonyl radical CO or a radical —$CHR^4$; and $R^4$ is an OH group, a hydroxyl group which may be acylated by $C_2$–$C_4$-acyl, or a chlorine atom;

or an agriculturally customary salt of a compound I.

2. The isoxazol-4-ylbenzoyl compound of the formula I as defined in claim 1, wherein the radical

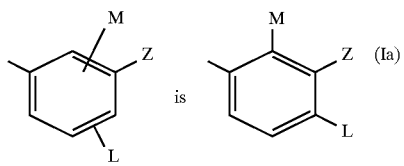 is 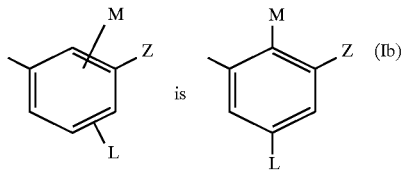 (Ia)

and where

L is $C_1$–$C_6$-alkyl, $C_2$–$C_6$-alkenyl, $C_2$–$C_6$-alkynyl, $C_1$–$C_4$-alkoxy, $C_1$–$C_4$-alkylthio, $C_1$–$C_4$-haloalkyl, $C_1$–$C_4$-haloalkoxy, $C_1$–$C_4$-haloalkylthio, $C_1$–$C_4$-alkylsulfonyl, halogen, nitro or cyano and M is hydrogen $C_1$–$C_6$-alkyl, $C_2$–$C_6$-alkenyl, $C_2$–$C_6$-alkynyl, $C_1$–$C_4$-alkoxy, $C_1$–$C_4$-alkylthio, $C_1$–$C_4$-haloalkyl, $C_1$–$C_4$-haloalkoxy, $C_1$–$C_4$-haloalkylthio, $C_1$–$C_4$-alkylsulfonyl, halogen, nitro or cyano.

3. The isoxazol-4-ylbenzoyl compound of the formula I as defined in claim 1, wherein the radical

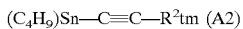 is 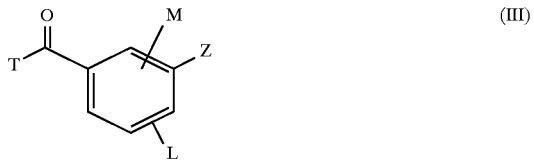 (Ib)

and where

L and M are $C_1$–$C_6$-alkyl, $C_2$–$C_6$-alkenyl, $C_2$–$C_6$-alkynyl, $C_1$–$C_4$-alkoxy, $C_1$–$C_4$-alkylthio, $C_1$–$C_4$-haloalkyl, $C_1$–$C_4$-haloalkoxy, $C_1$–$C_4$-haloalkylthio, $C_1$–$C_4$-alkylsulfonyl, halogen, nitro or cyano.

4. The isoxazol-4-ylbenzoyl compound of the formula I as defined in claim 1, where the radicals L or M are hydrogen, methyl, methoxy, methylthio, chlorine, cyano, methylsulfonyl, nitro or trifluoromethyl.

5. A process for the preparation of the isoxazol-4-ylbenzoyl compound of the formula I as defined in claim 1, where Q is a radical CO—J, which comprises reacting alkynyl stannates of the formula A2

$(C_4H_9)Sn$—$C\equiv C$—$R^2tm$ (A2)

with a benzoic acid of the formula III

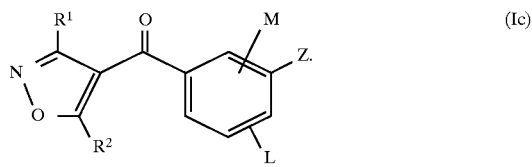 (III)

where T is halogen, to give benzoylalkynes of the formula B2

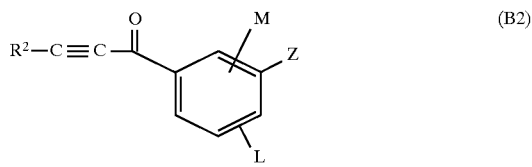 (B2)

and subjecting these benzoylalkenes together with nitrile oxides of the formula C2

 (C2)

where $R^1$ is $C_1$–$C_4$-alkyl to a cycloaddition reaction to give the isoxazoles of the formula Ix (Ic)

6. A herbicidal composition comprising at least one isoxazol-4-ylbenzoyl compound of the formula I as defined in claim 1 and customary inert additives.

7. A method of controlling undesirable vegetation, which comprises allowing a herbicidally active amount of a isoxazol-4-ylbenzoyl compound of the formula I as defined in claim 1 to act on the plants or their environment.

8. An isoxazol-4-ylbenzoyl compound of the formula I as defined in claim 1, where Z is a 5- to 6-membered heteroaromatic ring which has one to three hetero atoms selected from the group consisting of oxygen, sulfur or nitrogen and which is unsubstituted or substituted by halogen, cyano, nitro, $C_1$–$C_4$-alkyl, $C_1$–$C_4$-haloalkyl, $C_3$–$C_6$-cycloalkyl, $C_1$–$C_4$-alkoxy, $C_1$–$C_4$-haloalkoxy, $C_1$–$C_4$-alkylthio, $C_1$–$C_4$-haloalkylthio, di-$C_1$–$C_4$-alkylamino or phenyl which is unsubstituted or substituted by halogen, cyano, nitro, $C_1$–$C_4$-alkyl or $C_1$–$C_4$-haloalkyl, or is a benzo-fused fivehaloalkylthio, - or six-membered heteroaromatic ring which is unsubstituted or substituted by halogen, cyano, nitro, $C_1$–$C_4$-alkyl or $C_1$–$C_4$-haloalkyl.

* * * * *

UNITED STATES PATENT AND TRADEMARK OFFICE
CERTIFICATE OF CORRECTION

PATENT NO.: 5,834,402

DATED: November 10, 1998

INVENTOR(S): VON DEYN et al.

It is certified that error appears in the above-identified patent and that said Letters Patent is hereby corrected as shown below:

Col. 33, claim 5, line 44, "$(C_4H_9)Sn-C{\equiv}C-R^2tm$ (A2)" should be:
  --$(C_4H_9)Sn-C{\equiv}C-R^2$     (A2)--.

Col. 34, claim 5, line 10, "benzoylalkenes" should be --benzoylalkynes--.

Col. 34, claim 5, line 18, "formula Ix" should be --formula Ic--.

Col. 34, claim 8, line 41, "hetero atoms" should be --heteroatoms--.

Col. 34, claim 8, line 42, "or" should be --and--.

Col. 34, claim 8, line 49, "fivehaloalkylthio, -" should be --five- --.

Signed and Sealed this

Twenty-fifth Day of May, 1999

Attest:

Q. TODD DICKINSON

*Attesting Officer*     *Acting Commissioner of Patents and Trademarks*